United States Patent
Troxell et al.

(10) Patent No.: US 12,290,633 B2
(45) Date of Patent: May 6, 2025

(54) SYSTEMS AND METHODS FOR ADAPTIVE COUGH DETECTION AND ADAPTIVE MECHANICAL INSUFFLATION-EXSUFFLATION (MI-E) THERAPY

(71) Applicant: KONINKLIJKE PHILIPS N.V., Eindhoven (NL)

(72) Inventors: David Aaron Troxell, San Luis Obispo, CA (US); Seunghyun Lee, Valrico, FL (US); Jon Nilsestuen, Friendswood, TX (US)

(73) Assignee: Koninklijke Philips N.V., Eindhoven (NL)

( * ) Notice: Subject to any disclaimer, the term of this patent is extended or adjusted under 35 U.S.C. 154(b) by 666 days.

(21) Appl. No.: 17/399,249

(22) Filed: Aug. 11, 2021

(65) Prior Publication Data
US 2022/0047830 A1    Feb. 17, 2022

Related U.S. Application Data

(60) Provisional application No. 63/066,572, filed on Aug. 17, 2020.

(51) Int. Cl.
  *A61M 16/00* (2006.01)
  *G05B 19/042* (2006.01)
  *G16H 40/63* (2018.01)
(52) U.S. Cl.
  CPC ...... *A61M 16/024* (2017.08); *A61M 16/0006* (2014.02); *A61M 16/0069* (2014.02);
  (Continued)

(58) Field of Classification Search
  CPC ............ A61M 16/024; A61M 16/0069; A61M 16/0009; A61M 16/003; A61M 16/0003;
  (Continued)

(56) References Cited

U.S. PATENT DOCUMENTS 5,345,930 A * 9/1994 Cardinal .......... A61M 16/0009
                                              128/205.24
6,929,007 B2 8/2005 Emerson
(Continued)

FOREIGN PATENT DOCUMENTS

CN     110038198 A     7/2019

OTHER PUBLICATIONS

Johnson et al. "Use of reactance to estimate transpulmonary resistance". Feb. 2, 2005, Eur Respir J; 25: 1061-1069 (Year: 2005).*
(Continued)

*Primary Examiner* — Timothy A Stanis
*Assistant Examiner* — Sara K Toich
(74) *Attorney, Agent, or Firm* — Daniel H. Brean

(57) ABSTRACT

A mechanical ventilation system comprises a mechanical ventilator configured to deliver ventilation to a patient. An electronic controller is programmed to control the mechanical ventilator to perform a mechanical insufflation-exsufflation (MI-E) therapy method including performing a MI-E cycle including: (i) during an insufflation cycle, delivering pressure to the patient at a positive insufflation gauge pressure; (ii) during an exsufflation cycle following step (i), delivering pressure to the patient at a negative exsufflation gauge pressure and detecting whether an upper airway collapse occurs; and (iii) reducing a magnitude of the negative exsufflation gauge pressure if an upper airway collapse is detected in step (ii).

11 Claims, 24 Drawing Sheets

(52) U.S. Cl.
CPC ............ *G05B 19/042* (2013.01); *G16H 40/63* (2018.01); *A61M 2016/0027* (2013.01); *A61M 2205/3341* (2013.01); *A61M 2230/40* (2013.01); *G05B 2219/25255* (2013.01)

(58) Field of Classification Search
CPC .. A61M 2016/0042; A61M 2016/0027; A61M 2016/003; A61M 2230/42; A61M 2205/332; A61M 2205/3331; A61M 2205/3334; A61M 2205/3365; A61B 5/091; A61B 5/087
See application file for complete search history.

(56) References Cited

U.S. PATENT DOCUMENTS

| | | | |
|---|---|---|---|
| 7,096,866 B2 | 8/2006 | Eliezer | |
| 9,320,863 B2 | 4/2016 | Balko | |
| 10,335,564 B2 | 7/2019 | Lee | |
| 2005/0061318 A1* | 3/2005 | Faram | A61M 16/0096 128/204.21 |
| 2007/0186928 A1 | 8/2007 | Eliezer | |
| 2013/0269698 A1 | 10/2013 | Balko | |
| 2016/0228660 A1* | 8/2016 | Lee | A61M 16/0009 |

OTHER PUBLICATIONS

Andersen et al. "Laryngeal response patterns influence the efficacy of mechanical assisted cough in amyotrophic lateral sclerosis" (Year: 2016).*

Chatwin et al "Airway clearance techniques in neuromuscular disorders: A state of the art review" (Year: 2017).*

Bach, J.R. "Criteria for extubation and tracheostomy tube removal for patients with ventilatory failure. A different approach to weaning." Chest 1996;110:1566-71.

Bach, JR. "Prevention of pulmonary morbidity for patients with Duchenne Muscular dystrophy." Chest 1997; 112(4):1024-1028.

Simonds, A. "Progress in respiratory management of bulbar complications of motor neuron disease/amyotrophic lateral sclerosis." Thorax Mar. 2017 vol. 72, No. 3.

Andersen, T. et al., "Laryngeal response patterns influence the efficacy of mechanical assisted cough in amyotrophic lateral sclerosis." Thorax 2016;0:1-9.

Sancho, J. et al., "Efficacy of mechanical insufflation-exsufflation in medically stable patients with amyotrophic lateral sclerosis". Chest 2004;125(4):1400-1405.

Andersen, T. et al., "Laryngeal Responses to Mechanically Assisted Cough in Progressing Amyotrophic Lateral Sclerosis." Resp Care May 2018;63(5):538-549.

Esquinas, A.M. et al. "Considerations about the effect of cough assist on Laryngeal Function in Neurologic Disease." Letter to the editor. Respir Care Nov. 2018;63(11):1459.

Eckert, D.J. et al. "Phenotypic approaches to obstructive sleep apnea—New pathways for targeted therapy." Sleep Medicine Review, 2018: 45-49.

Cao, Y. et al., "Phasic respiratory modulation of pharyngeal collapsibility via neuromuscular mechanisms in rats." J. Appl Physiol 2012;112(5):695-703.

Chatwin, M, et al., "Airway Clearance techniques in neuromuscular disorders: A state of the art review." Respiratory Medicine 2018;13: 98-110.

Striegl, A.M. et al., "Use of a lung model to assess mechanical in-exsufflator therapy in infants with tracheostomy." Pediatr Pulmonol 2011;46(3):211-217.

International Search Report for PCT/EP2021/071711 filed Aug. 4, 2021.

* cited by examiner

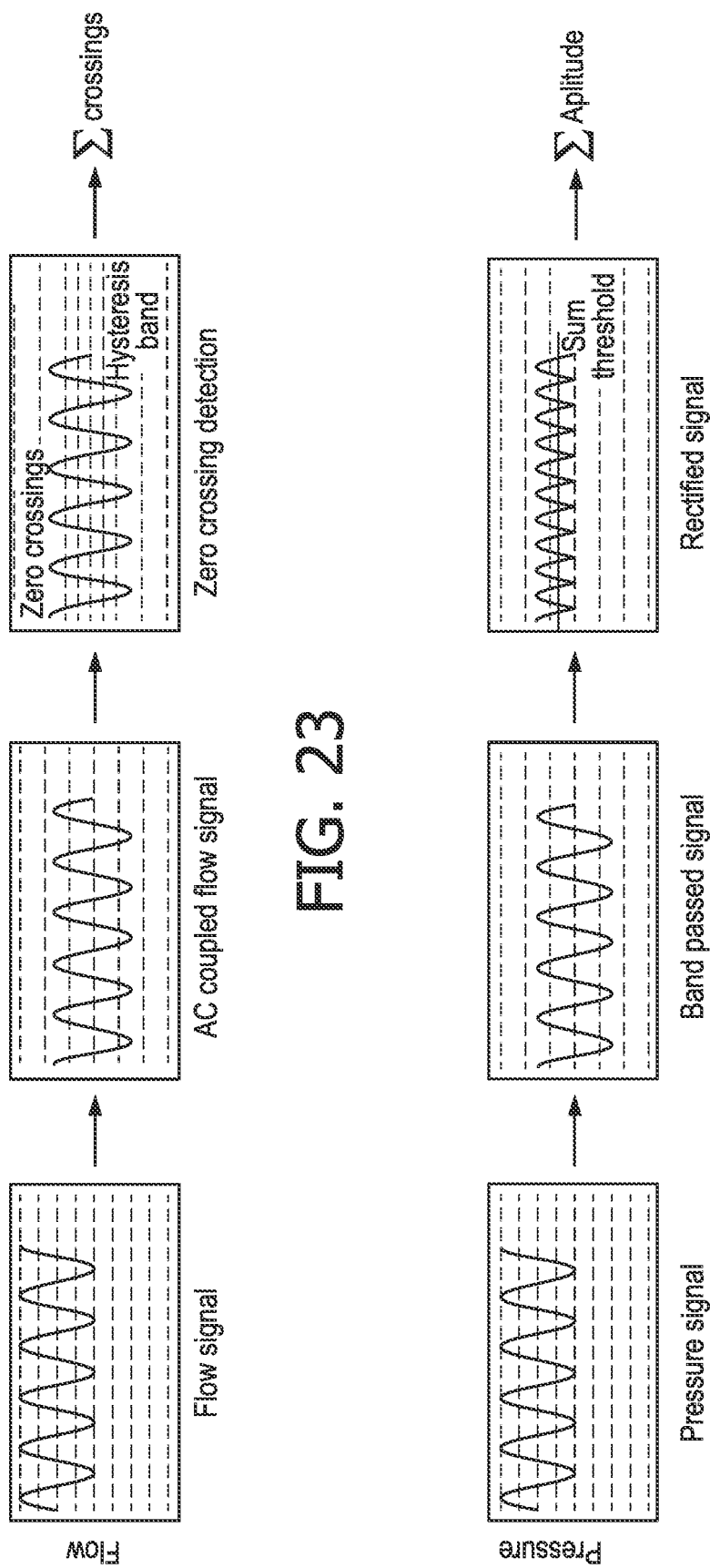

SYSTEMS AND METHODS FOR ADAPTIVE COUGH DETECTION AND ADAPTIVE MECHANICAL INSUFFLATION-EXSUFFLATION (MI-E) THERAPY

CROSS-REFERENCE TO RELATED APPLICATIONS

This patent application claims the priority benefit under 35 U.S.C. § 119(e) of U.S. Provisional Application No. 63/066,572, filed on Aug. 17, 2020, the contents of which are herein incorporated by reference.

The following relates generally to the ventilation therapy arts, and in particular to Mechanical Insufflation Exsufflation (MI-E) therapy and related arts.

BACKGROUND

Mechanical Insufflation Exsufflation (MI-E) therapy has been utilized in secretion management since the early 1950s. MI-E therapy was designed to augment a weakened or ineffective cough in patients with a neuromuscular disease (NMD) or in high spinal cord injuries where there is significant denervation of the primary respiratory muscles. MI-E therapy is delivered non-invasively through a face-mask or mouthpiece or through a tracheostomy or endotracheal adapter when needed.

MI-E aids in pulmonary secretion clearance by applying positive air pressure during inspiration (insufflation) to produce a large volume of air (targeting inspiratory capacity), then rapidly shifting to negative pressure (exsufflation) to create a pressure gradient that increases expiratory flow rates. Clinical evidence points to a peak expiratory flow (PEF; also referred to as peak expiratory flow rate, PEFR) or peak cough flow (PCF) critical threshold of 160 lpm for effective secretion clearance (see, e.g., Bach J R, Saporito L R. Criteria for extubation and tracheostomy tube removal for patients with ventilatory failure. A different approach to weaning. Chest 1996; 110:1566-71). For patients with NMD, MI-E is recommended once their PCF begins to drop below 270 l/min in order to help support their declining muscle strength and assist the patient in acclimating to the device (see, e.g., Bach J R, Ishikawa, Kim H. Prevention of pulmonary morbidity for patients with Duchenne Muscular dystrophy. Chest 1997; 112(4):1024-1028).

Patients with amyotrophic lateral sclerosis (ALS) are considered a prime target for inclusion of MI-E therapy as part of the overall respiratory support strategy. ALS is associated with loss of motor neurons in the cortex, brainstem, and spinal cord which results in muscle weakness and atrophy. Approximately 20-30% of patients diagnosed with ALS have bulbar symptoms at onset, however virtually all the remaining 70-80% of ALS patients will develop bulbar symptoms with disease progression (see, e.g., Simonds A. Progress in respiratory management of bulbar complications of motor neuron disease/amyotrophic lateral sclerosis. Thorax March 2017 Vol 72 No 3). Bulbar symptoms include dysarthria, dysphagia, difficulties clearing oropharyngeal secretions, impaired cough, choking laryngospasm, and aspiration. There is cumulative evidence supporting that MI-E therapy improves PCF and in combination with non-invasive ventilation (NIV) can prolong survival in ALS. However, in patients with bulbar ALS, the therapy has proven to be much less effective. In these patients the application of negative pressure during the exhalation phase of MI-E therapy results in upper airway collapse (see, e.g., Anderson T et al. Laryngeal response patterns influence the efficacy of mechanical assisted cough in ALS. Thorax 2016; 0:1-9; Sancho J, Servera E, Diaz J, Marin J. Efficacy of mechanical insufflation-exsufflation in medically stable patients with amyotrophic lateral sclerosis. Chest 2004; 125(4):1400-1405) and often a choking sensation that renders the therapy ineffective and often intolerable.

Upper airway closure and compression have been described in clinical literature by such invasive methods as fiberoptic bronchoscopy (see, e.g., Anderson T, Sandnes A, Fondenes O, Nilsen R, Tysnes O B, Heimdal J H, et al: Laryngeal Responses to Mechanically Assisted Cough in Progressing Amyotrophic Lateral Sclerosis. Resp Care May 2018; 63(5):538-549).

The following discloses certain improvements to overcome these problems and others.

SUMMARY

In one aspect, a mechanical ventilation system comprises a mechanical ventilator configured to deliver ventilation to a patient. An electronic controller is programmed to control the mechanical ventilator to perform a MI-E therapy method including performing a MI-E cycle including: (i) during an insufflation cycle, delivering pressure to the patient at a positive insufflation gauge pressure; (ii) during an exsufflation cycle following step (i), delivering pressure to the patient at a negative exsufflation gauge pressure and detecting whether an upper airway collapse occurs; and (iii) reducing a magnitude of the negative exsufflation gauge pressure if an upper airway collapse is detected in step (ii).

In another aspect, a mechanical ventilation system comprises a mechanical ventilator configured to deliver ventilation to a patient. An electronic controller is programmed to control the mechanical ventilator to perform a MI-E therapy method including performing a MI-E cycle including: (i) during an insufflation cycle, delivering pressure to the patient at a positive insufflation gauge pressure; and (ii) during an exsufflation cycle following step (i), delivering pressure to the patient at a negative exsufflation gauge pressure; and (iii) analyzing one or more respiratory metrics of the patient during the delivery of the pressure to the patient at the negative exsufflation gauge pressure.

In another aspect, a non-transitory computer readable medium stores instructions by an electronic controller of a mechanical ventilator to control the mechanical ventilator to perform a MI-E therapy method including performing a MI-E cycle including: (i) during an insufflation cycle, delivering pressure to the patient at a positive insufflation gauge pressure; (ii) during an exsufflation cycle following step (i), delivering pressure to the patient at a negative exsufflation gauge pressure; (iii) reducing a magnitude of the negative exsufflation gauge pressure to zero during step (ii); and (iv) increasing a magnitude of the negative exsufflation gauge pressure during the delivery if an analysis predicts an upper airway collapse will not occur during the exsufflation cycle.

One advantage resides in enabling more extensive use of MI-E therapy by preventing upper airway collapses in patients.

Another advantage resides in providing a mechanical ventilator with a negative pressure process that adjusts a negative pressure to prevent upper airway collapse in patients.

Another advantage resides in providing a non-invasive method to adjust mechanical insufflation-exsufflation settings for a mechanical ventilator providing ventilation therapy to a patient.

Another advantage resides in providing non-invasive flow measurements of ventilation therapy provided to a patient regardless of whether the therapy is delivered in a clinical setting, rehabilitation setting, or home setting.

Another advantage resides in enabling more extensive use of MI-E therapy for treating patients with bulbar ALS.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIGS. 23 and 24 show curves for a patient produced by algorithms executed by another module of the system of FIG. 5.

DETAILED DESCRIPTION

Figure 1:
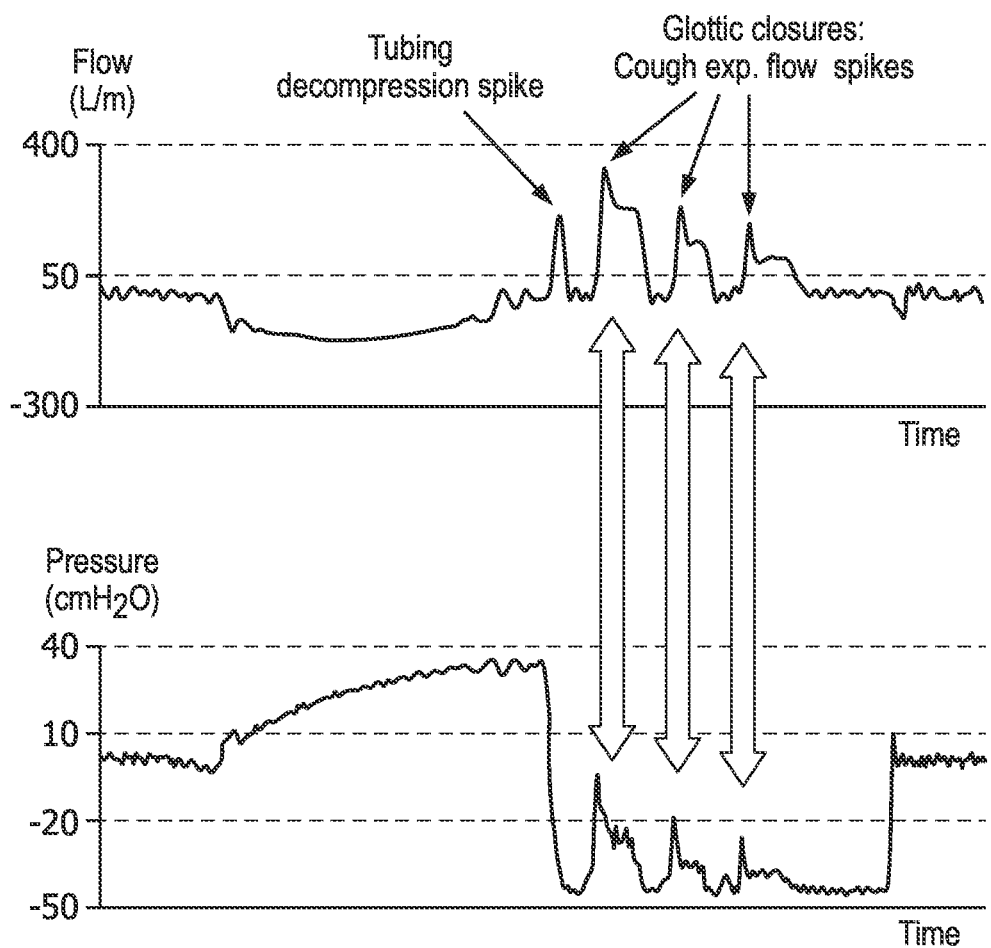
FIGS. 1-4 diagrammatically show flow and pressure graphs of a patient during cough assist therapy.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

Unless otherwise indicated, all pressure values herein are gauge pressure values, where zero pressure corresponds to atmospheric pressure.

Embodiments disclosed herein provide a way to assess upper airway response to MI-E therapy by evaluating the flow and pressure waveforms generated by an MI-E device (e.g., a Philips 70-series (i.e., CoughAssist) device available from Koninklijke Philips N.V.; Eindhoven, the Netherlands). The disclosed approaches advantageously address aspects of airway clearance therapy (ACT).

With reference to FIGS. 1-4, various flow pattern curves are shown for ALS patients. FIG. 1 shows a "normal" airway flow curve over time (top plot) and a "normal" airway pressure curve over time (bottom plot) of a patient with a cough. Following an initial gas decompression spike, three cough efforts are noted with simultaneous expiratory flow spikes and expiratory pressure spikes. The greatest peak cough flow (PCF) occurs with the first effort when lung and chest wall recoil pressures are greatest. ALS patients with bulbar symptoms present with two primary expiratory flow patterns that are related to the progression of the disease.

Figure 2:
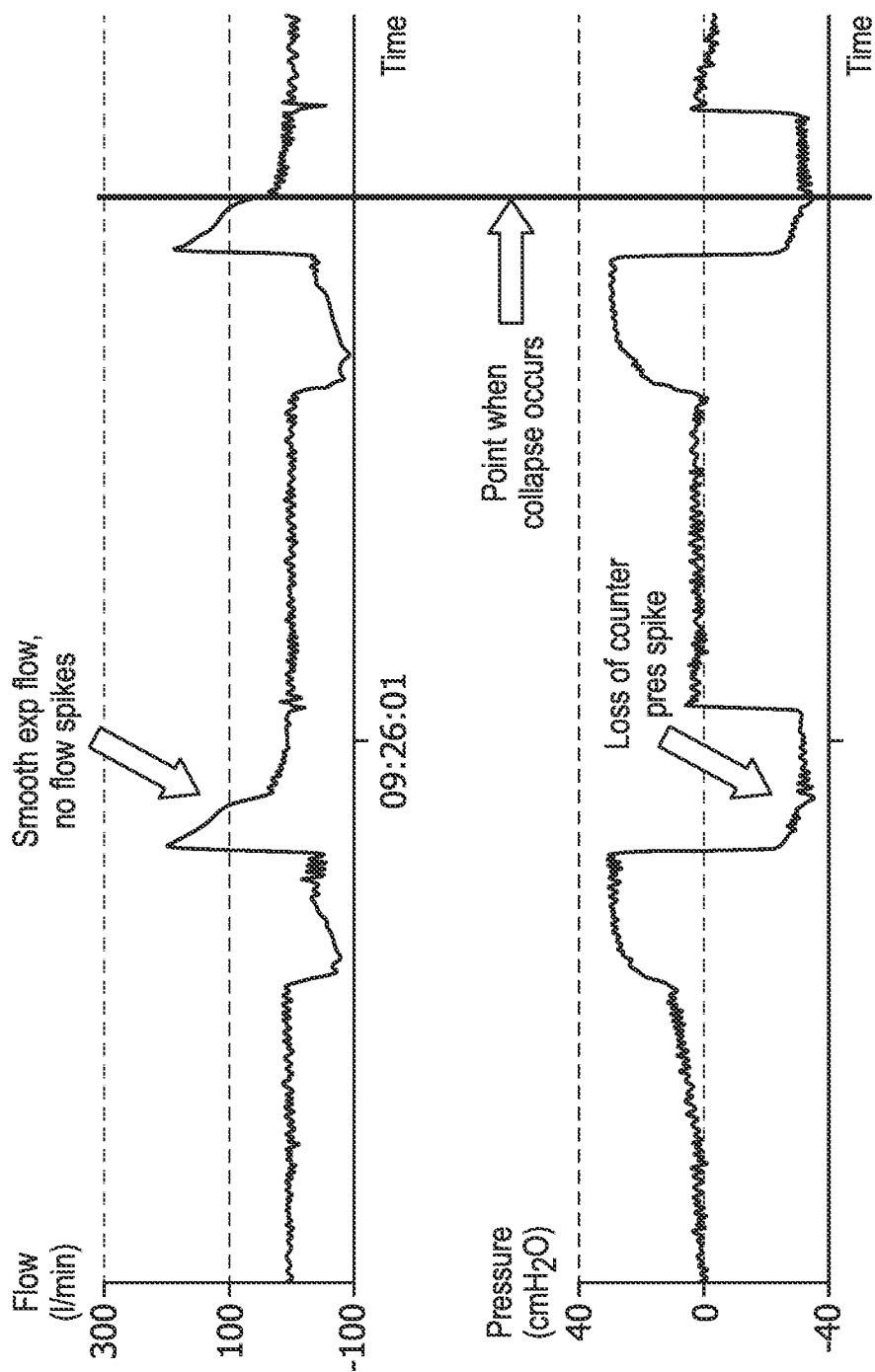

The first expiratory flow pattern, shown in FIG. 2, occurs earlier on in the progression of bulbar symptoms, and results in a loss of the ability for the patient to close the glottis (i.e., the patient is no longer able to create the compression phase of the cough, and no longer able to speak). As a result of the lost ability to cough, the expiratory flow pattern is smooth, rounded off, and there are no longer multiple expiratory flow spikes characteristic of normal cough efforts, as shown in FIG. 1. Simultaneously, the expiratory pressure spikes (also associated with glottic closure, as indicated by the double ended arrows in FIG. 1) are no longer apparent.

FIG. 2 shows that, in bulbar patients, as the patient loses the ability to close their glottis, the expiratory flow curve smooths out, representing loss of the compression phase of the cough. Also, as lung recoil pressure reduces and the negative pressure advances into the airway, at some point the upper airway collapses, and there is a sudden drop in the expiratory flow.

With regard to the initial loss of glottic control and the resulting smooth expiratory flow pattern shown in FIG. 2, the disclosed systems and methods are is designed to delay, or even prevent collapse of the upper airway during the negative pressure exhalation phase of MI-E therapy in patients with unstable upper airways. Mitigating upper airway collapse is accomplished by identifying significant flow decay following PEF that does not continue to gradually decay down to the zero or ambient flow condition during the allotted expiratory time (shown by the vertical line in FIG. 2). The abrupt reduction in expiratory flow may be addressed by using a servo controller to quickly reduce negative pressure to a point where exhaled flow continues to gradually decay to the zero-flow line during the set exhale time, as shown in FIG. 3.

Figure 3:
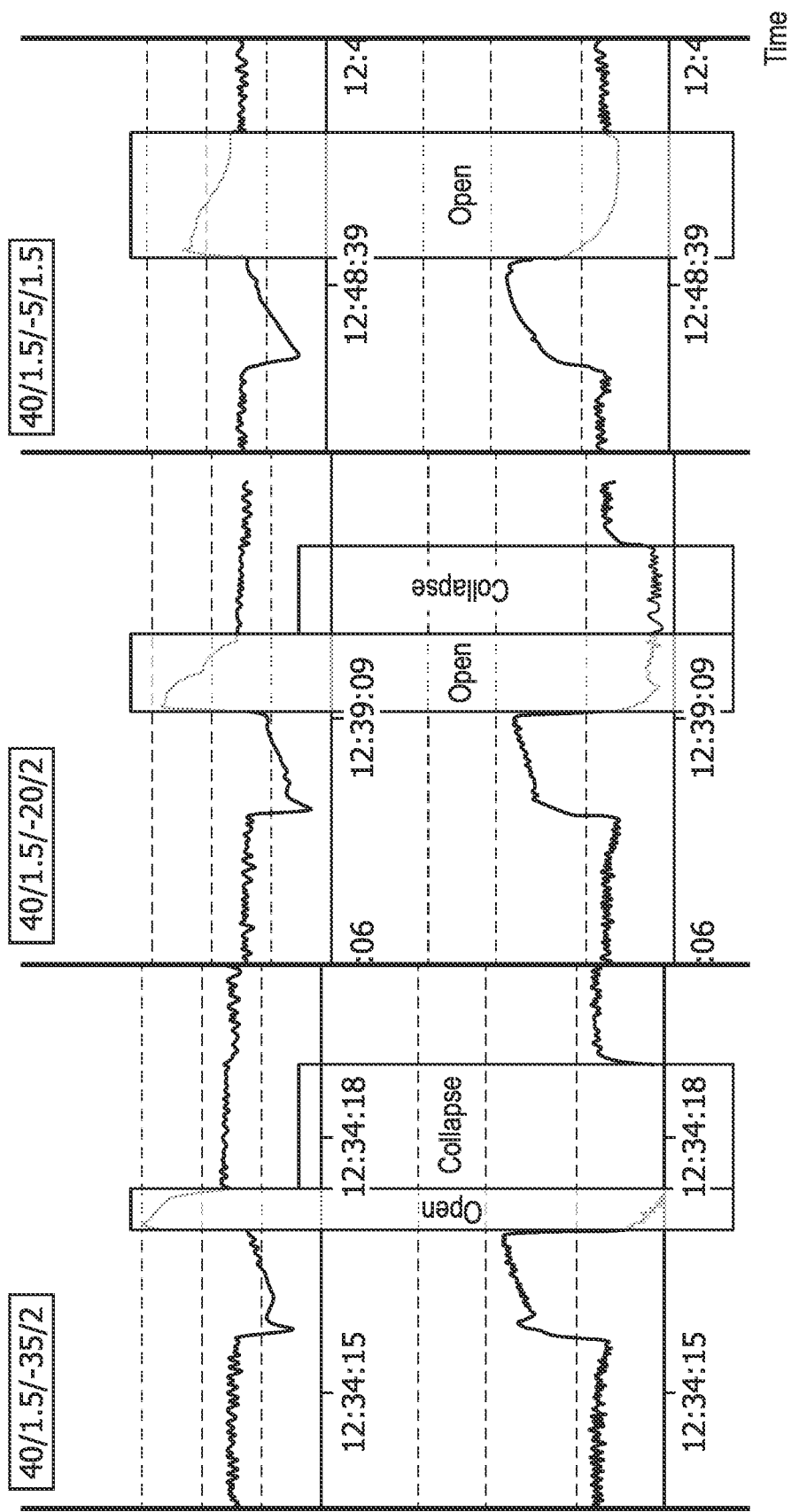

FIG. 3 illustrates an example of how manual titration of the negative pressure can extend the expiratory flow beyond the initial collapse point. The titration process adjusts the negative pressure to optimize it while avoiding upper airway collapse. While the example of FIG. 3 was a manual-sequential breath titration, as disclosed herein this process may be replaced by an automated process performed over several breaths, or by a rapid servo mechanism that can auto-titrate the negative pressure within a single breath (or several sequential breaths) replacing the manual titration process.

FIG. 3 shows pressure titration steps that were performed in 5 cmH$_2$O increments beginning at −40 cmH$_2$O, and progressing all the way to −5 cmH$_2$O. For brevity and space reasons only three of the pressure increments are displayed (−35 cmH$_2$O, −20 cmH$_2$O, and −5 cmH$_2$O). The Peak expiratory flow is highest at the first increment of −35 cmH$_2$O when the pressure gradient is highest (+40 cmH$_2$O to −35 cmH$_2$O) and slightly diminishes as the magnitude of the pressure is reduced. As a result of reducing the magnitude of the negative pressure the expiratory time during which flow occurs prior to the collapse progressively lengthens. After adding an active cough, the best PCF occurred at a pressure setting of −20 cmH$_2$O.

Figure 4:
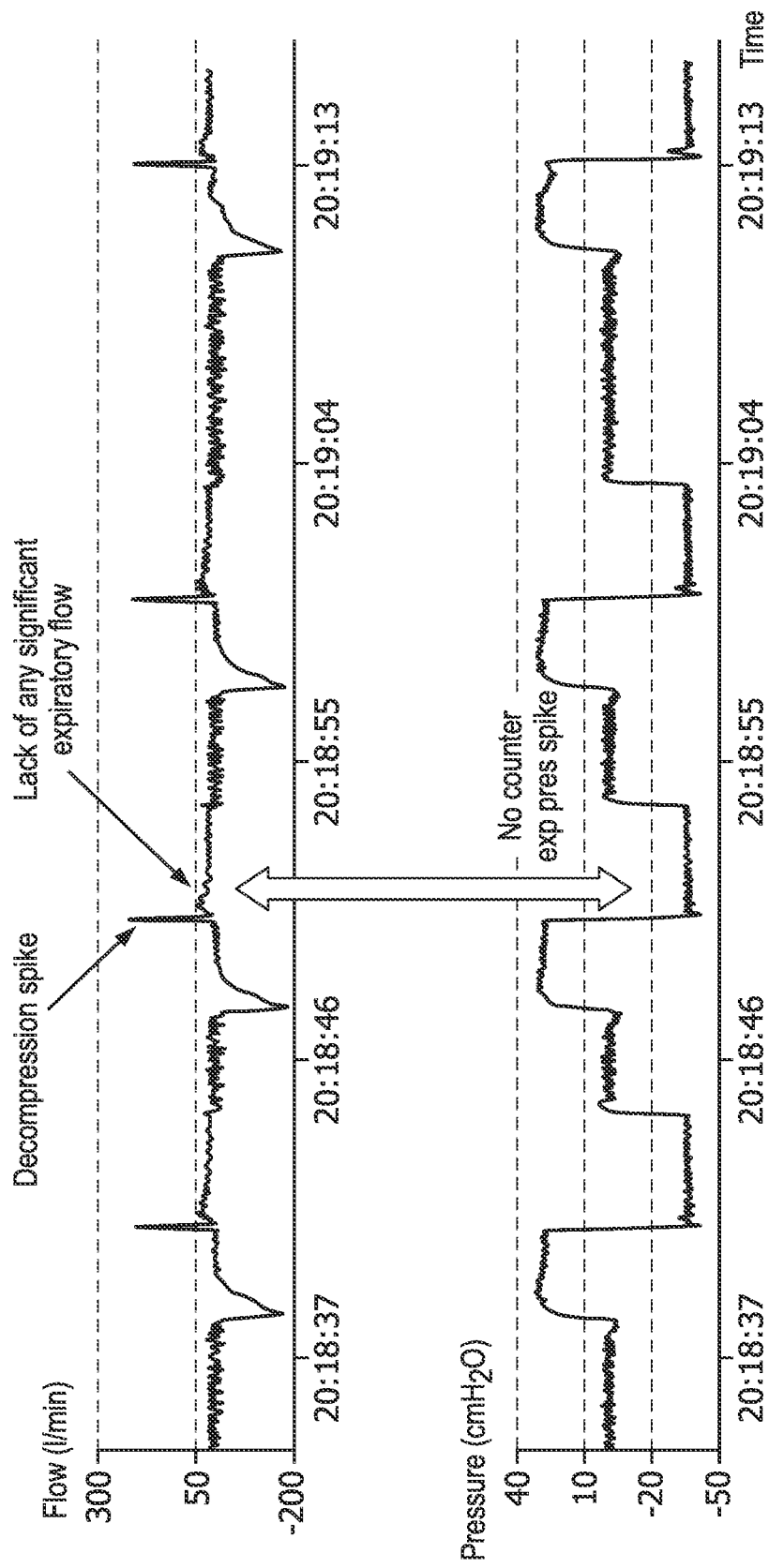

FIG. 4 shows a second expiratory flow pattern that appears later in a progression of bulbar symptoms and is characterized by a nearly complete loss of the expiratory flow curve (i.e., there is no longer a smooth expiratory flow pattern). Instead, FIG. 4 shows an initial gas decompression spike that is followed by a nearly flat expiratory flow curve, with little or no evidence of significant expiratory flow (not even passive flow). This characteristic is the result of complete loss of muscle tone in the upper airway and subsequent collapse when exposed to negative pressure during the exhale phase of MI-E. (To maximize algorithmic effectiveness, the auto titration to maximize the target inspiratory pressure occurs first. Increasing the Maximum Inspiratory Pressure increases lung and chest wall recoil pressure and moves the negative pressure point at which the collapse occurs.).

FIG. 4 shows that when there is complete loss of glottic control, the upper airway becomes susceptible to collapse when exposed to negative pressure. In FIG. 4, there is nearly complete collapse when the negative pressure is applied, and the expiratory flow trace is comprised of a gas decompression spike followed by a nearly flat expiratory flow curve.

Figure 5:
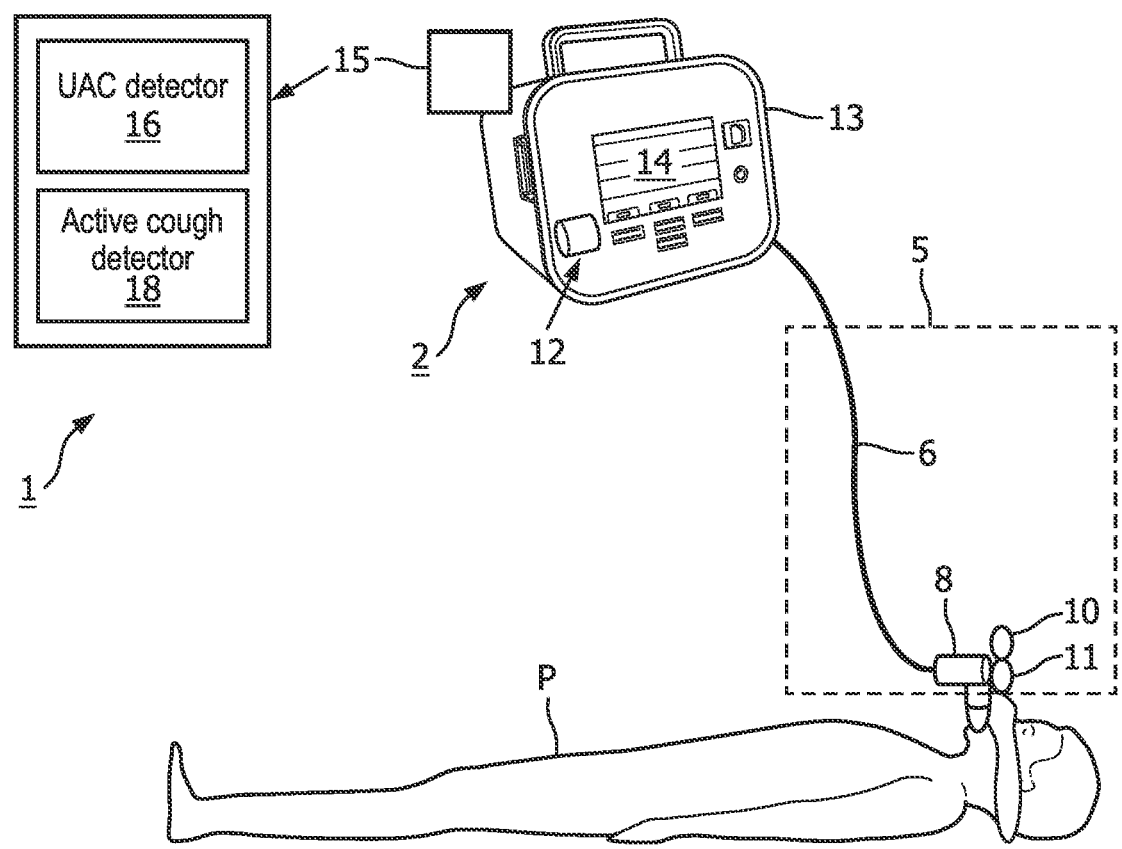
FIG. 5 diagrammatically shows an illustrative apparatus for ventilator systems in accordance with the present disclosure.

With reference to FIG. 5, a mechanical ventilator system 1 for providing ventilation therapy to an associated patient P is shown. As shown in FIG. 5, the system 1 includes a mechanical ventilator 2 configured to perform MI-E therapy. For example, the mechanical ventilator 2 may be a CoughAssist airway clearance device (available from Koninklijke Philips N.V.). The mechanical ventilator 2 includes an outlet (not shown) connected to a patient breathing circuit 5 to deliver mechanical ventilation to the patient P to perform MI-E therapy. The patient circuit 5 includes as an air hose 6, a patient port 8, and one or more breathing sensors, such as a gas flow meter 10, a pressure sensor or meter 11, an end-tidal carbon dioxide (etCO$_2$) sensor (not shown), and/or so forth. Alternatively, some or all of the sensors 10, 11 may be internal to the mechanical ventilator 2. The patient port 8 can be variously embodied. For non-invasive ventilation, the patient port 8 is suitably a mask strapped to the patient's face. For invasive ventilation, the patient port 8 may be an endotracheal tube, tracheostomy tube, or so forth.

The mechanical ventilator 2 includes an air inlet (not shown) to draw atmospheric air which is delivered to the air hose 6 to provide the MI-E therapy to the patient. For example, the ventilator 2 may include a blower 12 to deliver air to the air hose 6. (Note, the blower 12 is indicated diagrammatically in FIG. 5, as it is disposed inside the housing of the mechanical ventilator 2 and hence occluded from view). The mechanical ventilator 2 includes an electronic processor or electronic controller 13, a display 14, and a non-transitory computer readable medium 15 storing instructions executable by the electronic process 13 to perform a mechanical insufflation-exsufflation (MI-E) therapy method 100, 200, 300, 400, as described in more detail below.

Figure 6:
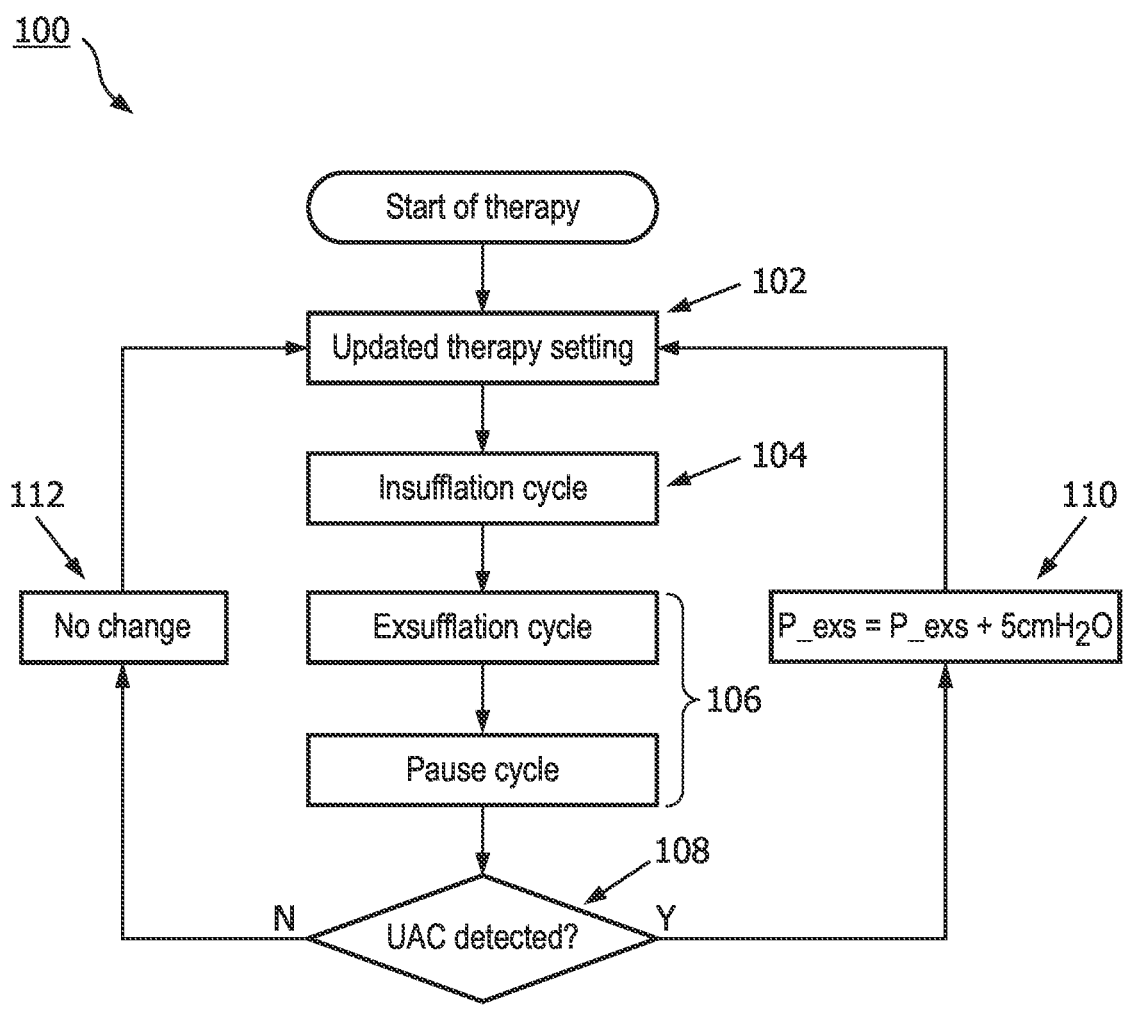
FIG. 6 shows an example flow chart of operations suitably performed by the system of FIG. 5.

With reference to FIG. 6, and with continuing reference to FIG. 5, an example embodiment of the MI-E therapy method 100 is diagrammatically shown as a flow chart. The MI-E therapy method 100 includes a titration protocol with a negative pressure protocol for eliminating upper airway collapse (UAC) over the course of one or more MI-E cycles. To begin the method 100, at an operation 102, ventilation therapy is delivered by the mechanical ventilator 2 to the patient P with a therapy setting. The therapy setting can be a target inspiratory pressure, which can be set to maximum value tolerated by the patient with the intent of maximizing inspiratory capacity (MIC). For example, a target inspiratory pressure can be 40 cmH$_2$O (gauge pressure) or slightly higher. While higher values of 60 cmH$_2$O or more have been reported in literature (see, e.g., Esquinnas A M, Fiorentino G. Considerations about the effect of Cough Assist on Laryngeal Function in Neurologic Disease. Letter to the editor. Respir Care Nov 2018; 63(11):1459), pulmonary physicians are reluctant to prescribe values much above 40 cmH$_2$O because of the potential risk of pneumothorax. In one example, where the target pressure was set to 50 cmH$_2$O in a DMD patient with pneumonia, the pressure setting resulted in a pneumothorax. Maximizing the target inspiratory pressure of the patient P can also maximize the lung recoil pressure that is supporting the positive luminal pressure for preventing upper airway collapse. In both normal subjects and in patients with severe bulbar impairment, the upper airway remains open and does not collapse when there is no application of negative pressure. Frequently, by completely removing the negative pressure and relying on just passive lung recoil, patients can reach PCF values above the level of 160 L/min required to support clearance. In addition, if patients use their expiratory muscles to support a cough, this further increases the PCF that they can achieve without a negative pressure phase.

At an operation 104, during an insufflation cycle, the mechanical ventilator 2 is configured to deliver pressure to the patient at a positive insufflation gauge pressure (i.e., the target inspiratory pressure set at the operation 102).

At an operation 106, during an exsufflation cycle following the insufflation cycle, the mechanical ventilator 2 is configured to deliver pressure to the patient at a negative exsufflation gauge pressure. For example, the negative exsufflation gauge pressure can be delivered in −5 cmH$_2$O increments, and the exsufflation can be paused after each increment.

At an operation 108, the negative pressure delivery operation 106 continues until an UAC is detected. In some embodiments, the patient P may be required to actively perform a cough or exhale once a UAC is detected.

This operation 108 can be performed in a variety of automated manners. In one example, the operation 108 includes measuring an airway flow rate of the patient P, using the flowmeter 10, at a predetermined time or time interval in the exsufflation cycle, and comparing the measured airway flow rate with a predetermined threshold to detect whether an UAC occurs. In another example, the operation 108 includes measuring a volume of air inhaled by the patient P, using the flowmeter 10, at a predetermined time in the exsufflation cycle 106, and comparing the measured volume of air with a predetermined threshold to detect whether an UAC occurs. In another example, the operation 108 includes measuring a rate of change of airway flow, using the flowmeter 10, at a predetermined time or time interval in the exsufflation cycle 106, and comparing the measured rate of change of airway flow with a predetermined threshold to detect whether an UAC occurs. In a further example, the operation 108 includes measuring a rotation rate of the blower 12 of the mechanical ventilator 2 at a predetermined time or time interval in the exsufflation cycle, and comparing the measured rotation rate of the blower with a predetermined threshold to detect whether an UAC occurs. In another example, the operation 108 includes measuring a pressure produced by the blower 12 at a predetermined time or time interval in the exsufflation cycle, and comparing the measured pressure produced by the blower with a predetermined threshold to detect whether an UAC occurs. In yet another example, the operation 108 includes measuring an airway flow rate of the patient using the flowmeter 10 and an airway pressure of the patient using the pressure meter 11, determining an airway reactance from the measured airway flow rate and the measured airway pressure; and detecting whether an UAC occurs based on the determined airway reactance. In another example, the operation 108 includes superimposing an ac oscillation on the pressure delivered to the patient P at the negative exsufflation gauge pressure. While superimposing the ac oscillation, a respiratory metric comprising (i) an airway flow rate of the patient can be measured using the flowmeter 10, or (ii) an airway pressure of the patient using the pressure meter 11. A UAC can be detected based in part on an ac component of the measured respiratory metric.

At an operation 110, a magnitude of the negative exsufflation gauge pressure is reduced if the UAC is detected at the UAC detection operation 108. More particularly, in illustrative operation 108 the exsufflation pressure for the next cycle, denoted $P_{-exs(next\ cycle)}$ is adjusted according to:

$$P_{-exs(next\ cycle)} = P_{-exs(last\ cycle)} + 5\ cmH_2O$$

where $P_{-exs\ (last\ cycle)}$ is the exsufflation pressure used in the last cycle. Note that since the $P_{-exs}$ values are negative gauge pressures, the +5 cmH$_2$O adjustment operates to reduce the magnitude of the (negative) gauge pressure. Thus, the negative exsufflation gauge pressure is reduced in magnitude by a predetermined pressure magnitude decrease increment, such as, for example, 5 cm H$_2$O. The operations 104-108 continue until no UAC is detected (illustrated in FIG. 6 as an operation 112). At the operation 112, the negative exsufflation gauge pressure at which no UAC is detected can be confirmed with delivering ventilation therapy to the patient P at the negative exsufflation gauge pressure at which no UAC is detected, 5 cm H$_2$O above this value, and 5 cm H$_2$O below this value to confirm the optimum gauge pressure.

In some embodiments, the MI-E method 100 can include detection of a critical closing pressure (Pcrit) value of the upper airway (see, e.g., Eckert et al. Phenotypic approaches to obstructive sleep apnea—New pathways for targeted therapy. Sleep Medicine Review, 2018: 45-49). This value would represent a patient specific starting point from which to begin the therapy delivery. In this example, the ventilation delivery process would be to reduce the magnitude of the negative pressure so that it was less than the Pcrit value and then verify opening of the upper airway.

The MI-E therapy method 100 is a dynamic process that is influenced by several opposing forces. In one example, a positive luminal pressure is defined as a combined elastic recoil forces of the lung and chest wall supported by the maximum target inspiratory pressure in support of keeping the airway open, and the patient's ability to supplement this force by their own active breath is a result of any expiratory muscle strength that they are capable of producing voluntarily. In another example, opposing the positive luminal pressure is a negative pressure imposed by the MI-E during the expiratory phase (defined as a negative luminal pressure).

Figure 7:
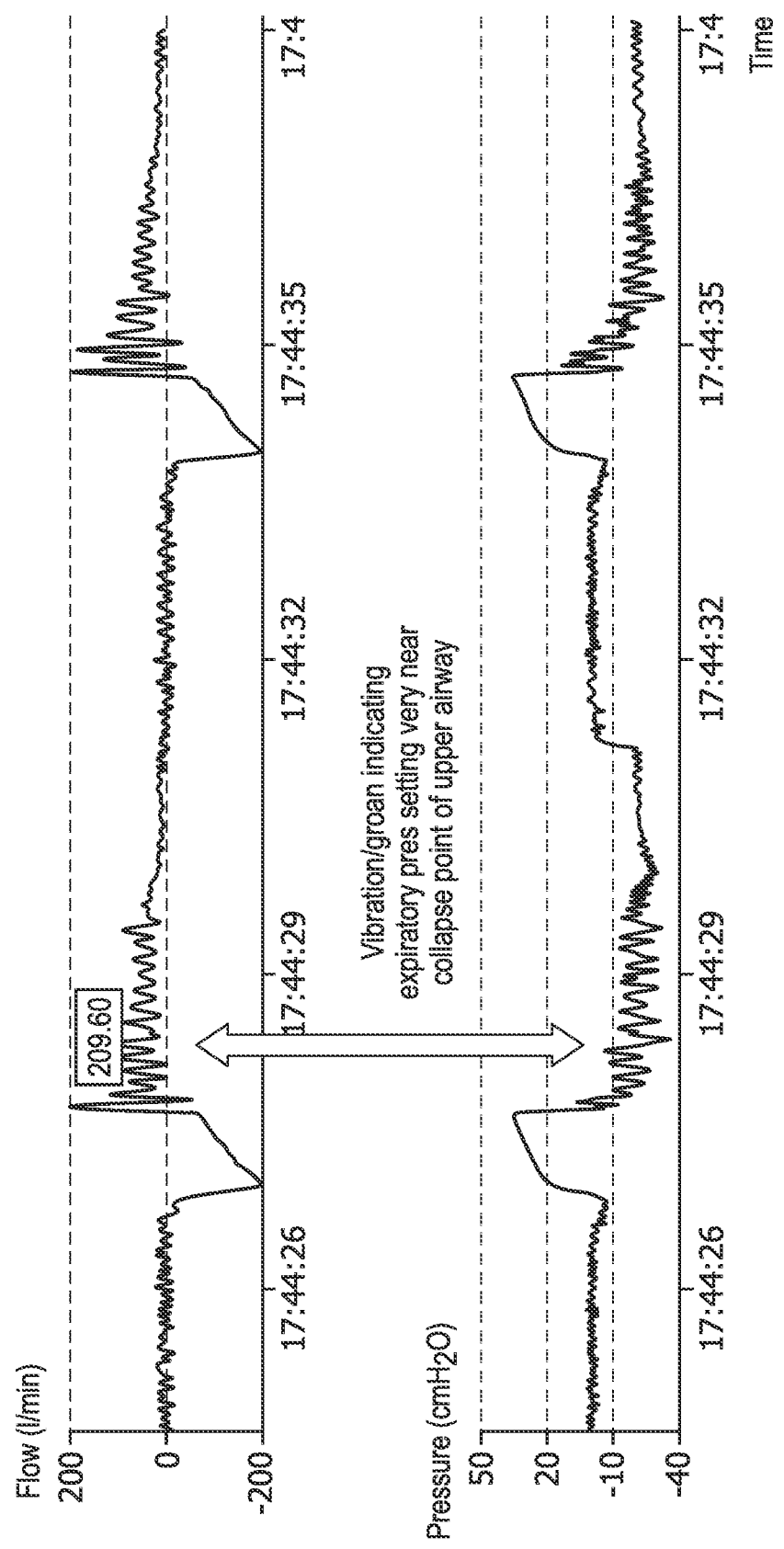
FIG. 7 shows flow and pressure curves for a patient undergoing the operations of FIG. 6.

As a consequence, when these two forces are nearly equal, the flaccid structures of the upper airway may vibrate, as shown in FIG. 7, and result in an expiratory groan that is audible and may be noticed by the patient, caregiver or clinician. This is a notable symptom and indicates that the current settings have resulted in a luminal pressure that is very close to the collapse point. Further reducing the magnitude of the negative pressure near this point should open the airway, silencing the vibration, relieving any uncomfortableness experienced by the patient and improving PCF. FIG. 7 shows a bulbar patient illustrating this vibration or groan.

Figure 8:
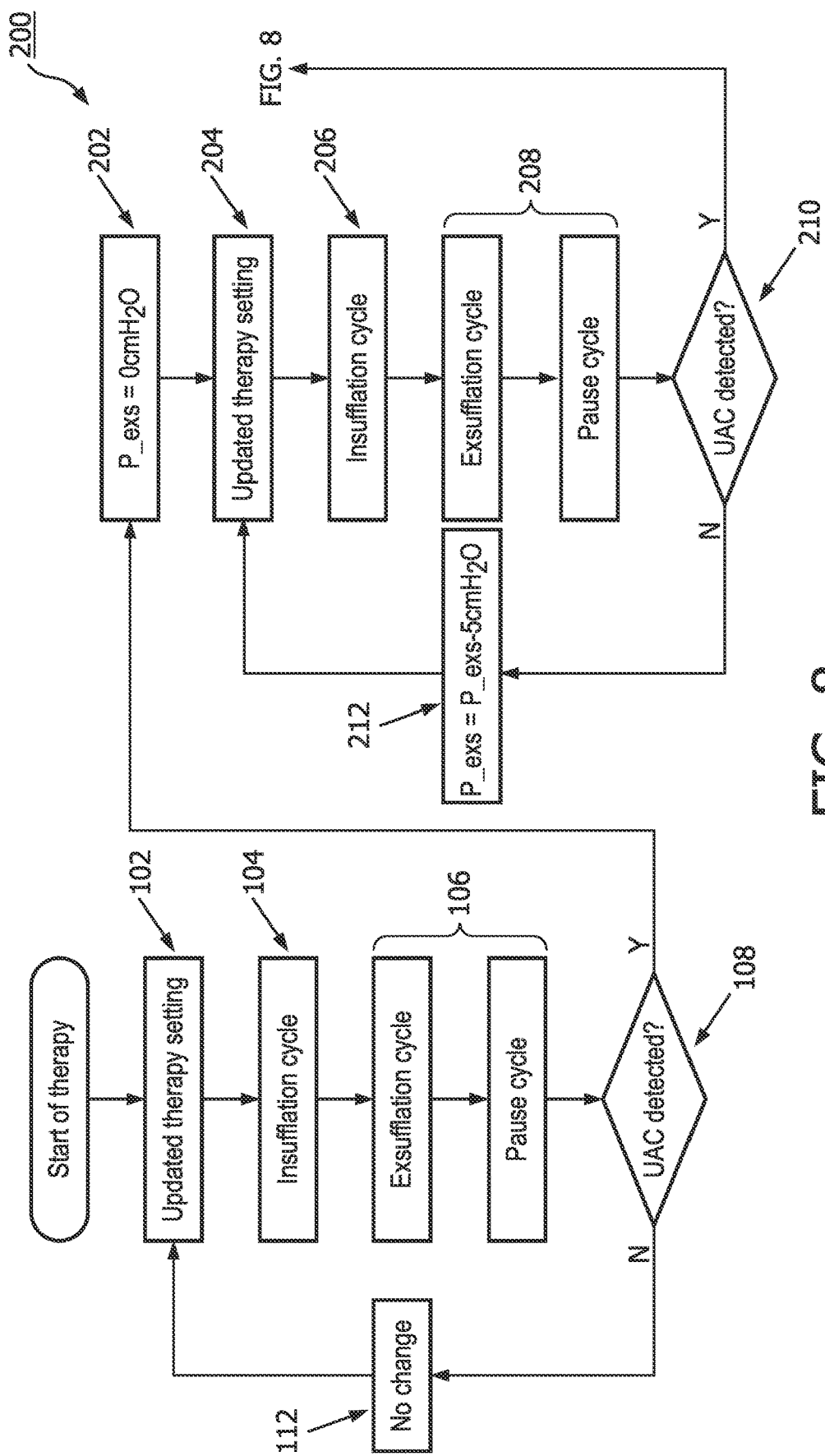
FIG. 8 shows another example flow chart of operations suitably performed by the system of FIG. 5.
Figure 8:
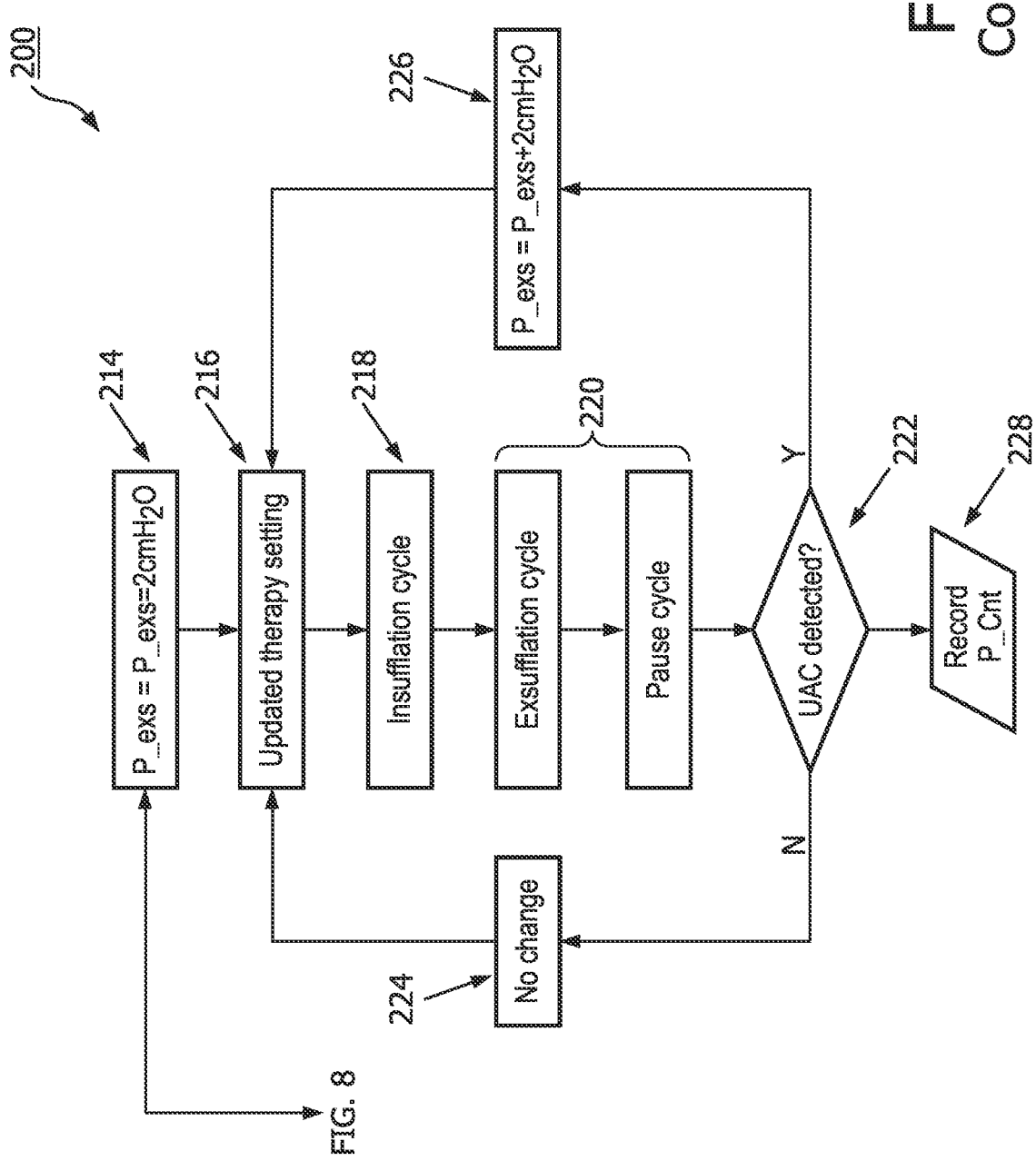

With reference to FIG. 8, and with continuing reference to FIGS. 5 and 6, an example embodiment of the MI-E therapy method 200 is diagrammatically shown as a flow chart. The MI-E therapy method 200 is similar to the MI-E therapy method 100 except as described below. The Mi-E therapy method 200 can include a stepwise reduction in the negative exsufflation gauge pressure.

The method 200 begins with the operations 102-108 as described above for the method 100. At the operation 108, if a UAC is detected, then the method 200 proceeds to an operation 202, in which the magnitude of the negative exsufflation gauge pressure is reduced to zero (as opposed to be reduced by a predetermined amount, as in the operation 110).

Once the magnitude of the negative exsufflation gauge pressure is reduced to zero, the method 200 proceeds with operations 204, 206, 208, and 210, which substantially correspond to the operations 102, 104, 106, and 108. At an operation 204, ventilation therapy is delivered by the mechanical ventilator 2 to the patient P with the updated therapy setting. At the operation 206, pressure is delivered to the patient P during an insufflation cycle at the positive insufflation gauge pressure. At the operation 208, pressure is delivered to the patient P during an exsufflation cycle at the negative exsufflation gauge pressure. At an operation 210, the negative pressure delivery operation 204 continues until an UAC is detected.

If a UAC is not detected at the operation 210, then at an operation 212, the magnitude of the negative exsufflation gauge pressure is increased. The magnitude of the negative exsufflation gauge pressure can be increased by a predetermined amount, such as by 5 cm H$_2$O. These operations 204-212 are repeated until the UAC is detected.

If a UAC is not detected at the operation 208, then at an operation 214, the magnitude of the negative exsufflation gauge pressure is decreased by a predetermined pressure magnitude decrease increment (such as, for example, 2 cm H$_2$O). After this increase, the method 200 proceeds to operations 216, 218, 220, and 222 (which substantially correspond to operations 204-210 and the details of which will not be repeated for brevity).

At the operation 222 (which corresponds to the UAC detection operation 210), if no UAC is detected, then at the operation 224, the magnitude of the negative exsufflation gauge pressure is maintained.

The operations 216-222 are repeated until a UAC is detected. Once a UAC is detected, the method 200 proceeds to the operation 226, in which the negative exsufflation gauge pressure is decreased by the predetermined pressure magnitude decrease increment (again, 2 cm H$_2$O).

At an operation 228, in addition to the operation 226 when the UAC is detected, the negative exsufflation gauge pressure is recorded as the negative exsufflation gauge pressure for a subsequent MI-E cycle of the MI-E therapy method (i.e., a Pcrit value).

Figure 9:
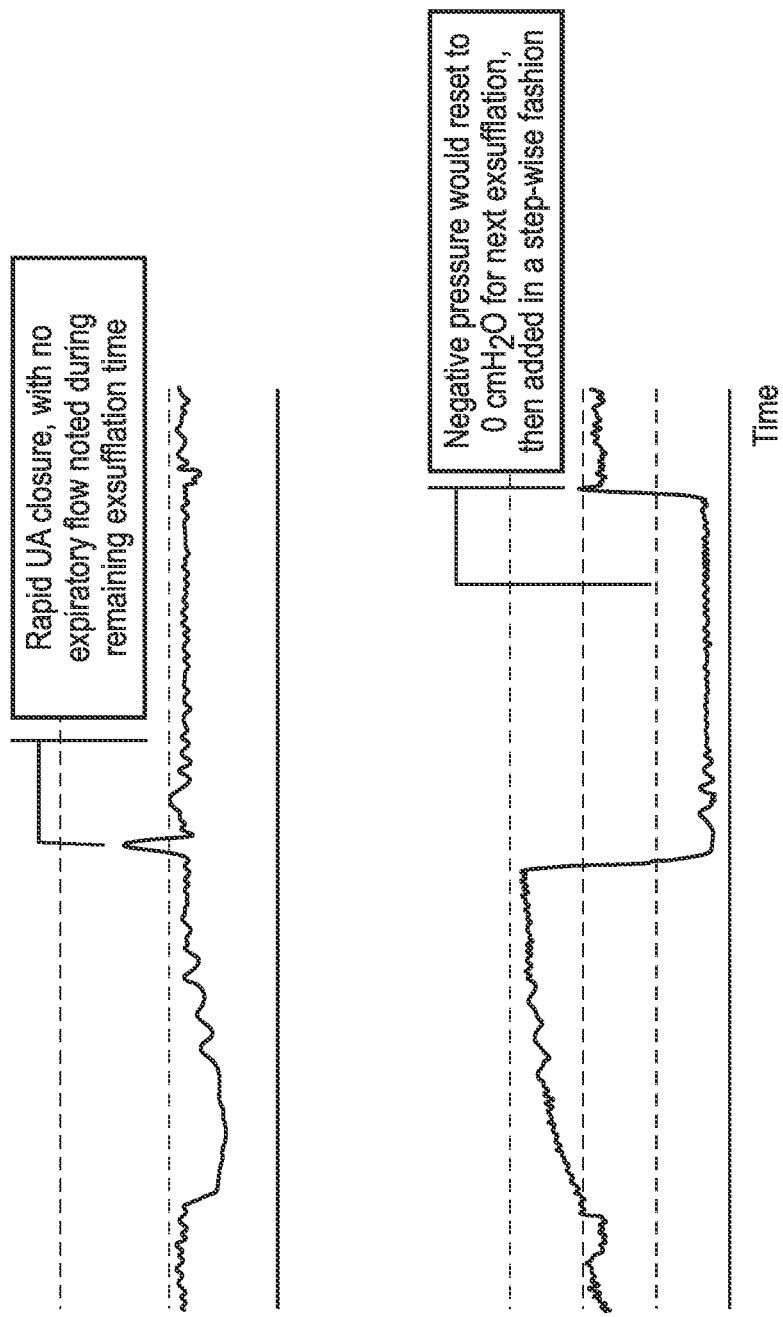
FIGS. 9 and 10 show flow and pressure curves for a patient undergoing the operations of FIG. 8.
Figure 10:
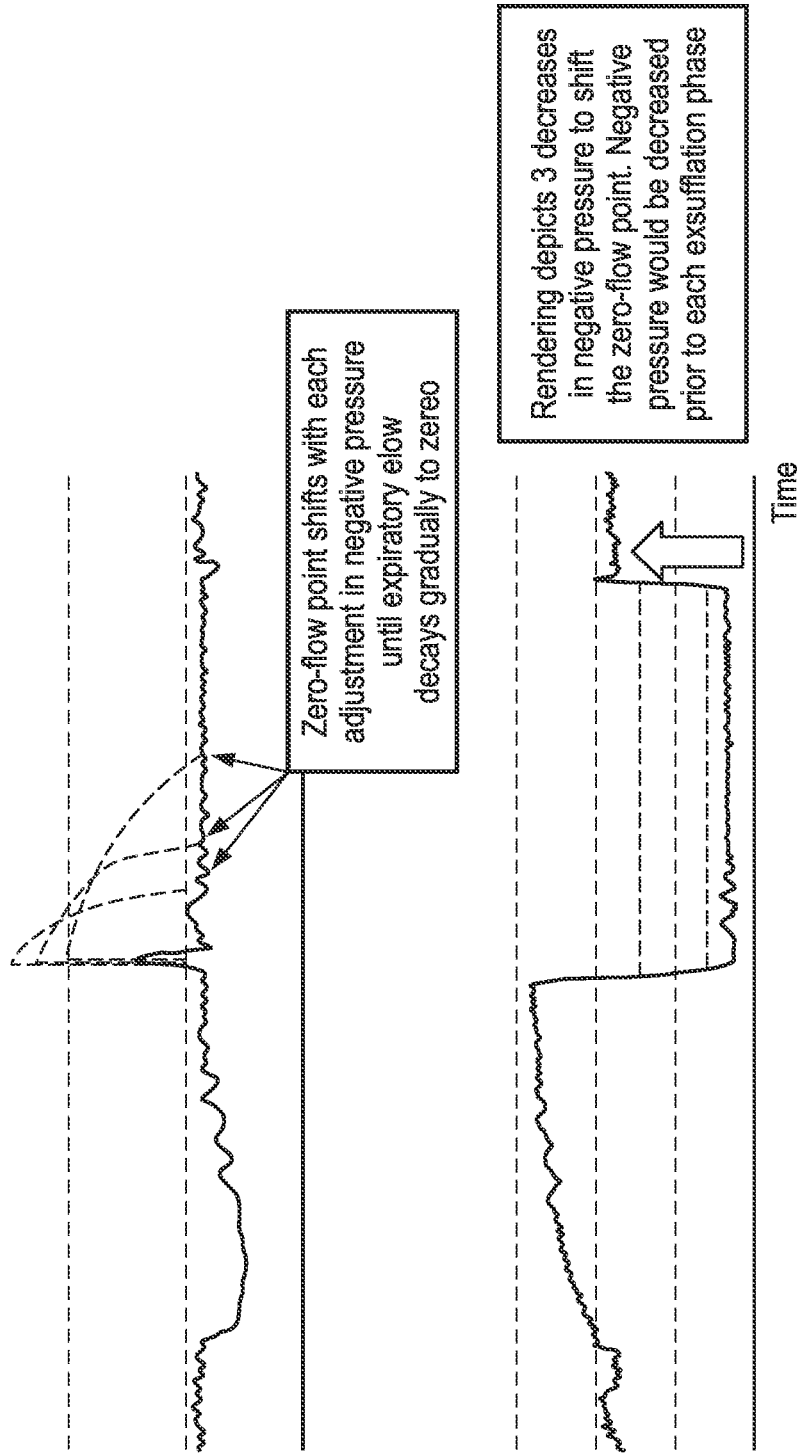

As noted, the method 200 can be considered a stepwise reduction in negative pressure over multiple exsufflation phases of the method 100. A trigger for the slow pressure response algorithm or process occurs when the zero-flow point (i.e., a UAC) occurs at the beginning of the exsufflation phase with no flow reversal to indicate an active cough effort with glottic closure, as shown in FIG. 9. Once triggered, the algorithm or process would reduce the negative pressure setting in increments of 5 cmH$_2$O prior to each exsufflation phase until the zero-flow point equals the exhale time setting. For example, if a fast UAC occurred with inhale and exhale pressures of +/−40 cmH$_2$O respectively, the electronic controller 13 would reduce the negative pressure setting to −35 cmH$_2$O prior to the next exsufflation phase and evaluate where the zero-flow point occurs. The negative pressure setting would continue to decrease towards ambient pressure until the zero-flow point equals the exhale time setting. FIG. 10 illustrates this negative pressure reduction.

In an alternative embodiment, a fast UAC can reset the negative pressure setting to 0 cmH$_2$O for the next delivered exsufflation phase. Once the negative pressure is set to ambient, each subsequent exsufflation phase would add −5 cmH$_2$O increasing the delivered/set negative pressure until a zero-flow point is predicted to occur prior to the end of exsufflation time. A zero-flow point prediction within exsufflation time creates the Pcrit negative pressure ceiling and stops any further addition of negative pressure. Once Pcrit is established, the negative pressure will be reduced by 2 cmH$_2$O setting a new negative pressure baseline. For example, Pcrit occurs at −25 cmH$_2$O, a new baseline negative pressure would be set at −23 cmH$_2$O.

In the embodiments of FIGS. 6 and 8, the titration of the negative pressure is performed over (typically) several MI-E cycles, with one adjustment of the negative pressure being made in each MI-E cycle. While this is effective, it can be unpleasant for the patient as he or she experiences (typically) multiple UAC events before the titration achieves a final negative pressure that provides effective MI-E therapy without inducing UAC events during the exsufflation cycle. In the following embodiments, a fast titration is performed within a single exsufflation cycle, by dynamically detecting in the initial phase of the exsufflation cycle whether a UAC collapse is likely to occur later in the cycle, and if so then reducing the magnitude of the negative pressure during that same exsufflation cycle in an effort to prevent the detected potential UAC collapse.

Figure 11:
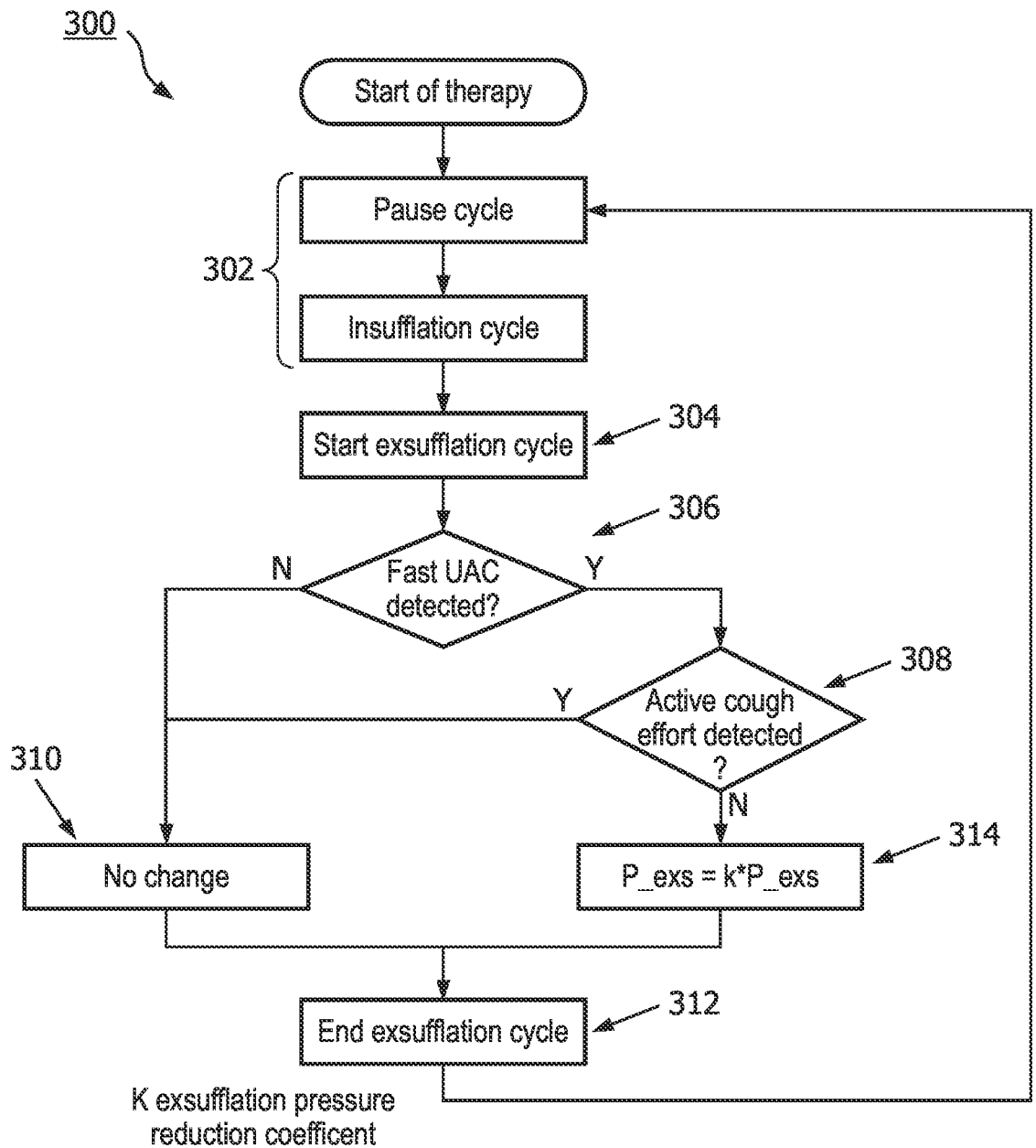
FIG. 11 shows another example flow chart of operations suitably performed by the system of FIG. 5.

With reference to FIG. 11, and with continuing reference to FIGS. 5-7, an example embodiment of the MI-E therapy method 300 is diagrammatically shown as a flow chart. The MI-E therapy method 300 is similar to the MI-E therapy method 100 except as described below.

At an operation 302, pressure is delivered to the patient P at a positive insufflation gauge pressure (similarly to the operations 104 and 206).

At an operation 304, after the insufflation cycle, pressure is delivered to the patient P at a negative exsufflation gauge pressure (similarly to the operations 106 and 208).

One or more respiratory metrics of the patient P are analyzed during the delivery of the pressure to the patient at the negative exsufflation gauge pressure. In one example, at an operation 306, the respiratory metric can include determining whether a fast UAC is occurring (similarly to the operations 108 and 210). If no fast UAC is detected (indicated at 310), then another iteration of the operations 302-306 occurs (indicated an operation 312). These operations are repeated until a fast UAC is detected.

In some examples, a UAC is determined largely by reaching a zero-flow point prior to the end of the exhale time phase and continuing at zero flow for the remainder of the exhale phase. Characterizing the cough effort facilitates differentiating between an active cough (i.e., glottis closure) and an UAC as both would have include a zero-flow point or a zero-crossing element. Various approaches can be used to differentiate between the two so as to accurately respond to true upper airway closure. For example, one way to do this is to ensure that there are at least two zero crossings to indicate that an individual is coughing (that is, a UAC is not occurring) and so the controller would not respond with a negative pressure reduction. Another is by introducing a brief time delay filter that introduces a brief pause once a zero-flow point occurred, so as to identify whether the zero-flow point is subsequently associated with flow reversal. If there is flow reversal, then the transient zero pressure point was created by glottis closure associated with a cough (not a UAC) and the controller would not respond with a negative pressure reduction. On the other hand, if the zero-pressure point were achieved, however no flow reversal was identified then this would meet the criteria for an UAC and the controller would respond with a reduction in negative pressure reduction.

In another example of analyzing the respiratory metrics of the patient P, at an operation 308, the respiratory metric can include a cough metric indicating whether the patient is coughing. If the cough metric indicates that the patient P is coughing, then no adjustment of the magnitude of the exsufflation pressure is made.

On the other hand, if the operation 306 indicates a likely impending UAC, and no coughing is detected at operation 308, then the method 300 continues to an operation 314, in which a magnitude of the negative exsufflation gauge pressure is reduced during the delivery of the (same) exsufflation cycle in an effort to prevent the predicted UAC from occurring. To do so, the magnitude of the negative exsufflation gauge pressure is multiplied by a constant k having a value of less than 1. The method 300 then proceeds to the operation 312 in which the operations 302-306 are repeated. In some cases, the exsufflation pressure adjustment at operation 314 may be sufficient to prevent the UAC predicted at operations 306, 308 from actually occurring in that exsufflation cycle. However, even if it is unable to prevent the UAC from occurring in that exsufflation cycle, each successive MI-E cycle will further reduce the exsufflation pressure by further passes of the operation 314. By making the adjustment during the same exsufflation cycle in which a UAC is predicted to occur, faster titration is achieved, and the patient is expected to experience fewer (and possibly no) actual UAC events.

Figure 12:
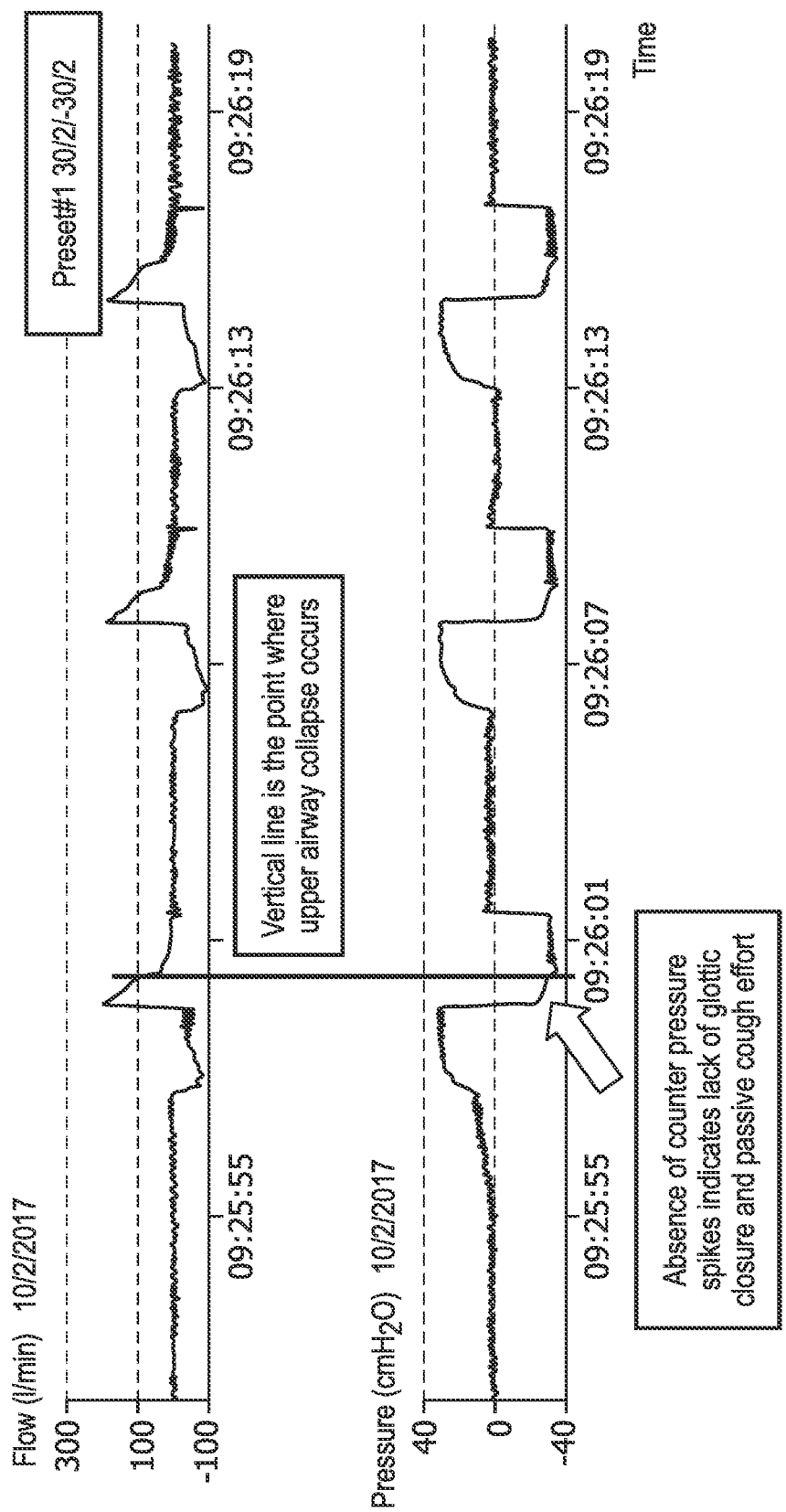
FIGS. 12-16 show flow and pressure curves for a patient undergoing the operations of FIG. 11.

The method 300 includes expiratory flow trace mapping to track and predict the expiratory zero-flow point based on the initial PEFR anchored by the expiratory time ($T_E$) setting in a breath-by-breath moving measurement window. In a patient profile that manifests an initial expiratory flow pattern with a relatively slow decay in PEFR (without glottic closure) indicating that a zero-flow point that will occur prior to the end of the exhale time (impending upper airway closure), the fast response algorithm or response of the method 300 would be triggered. A critical threshold for triggering the fast response algorithm of the method 300 would include an absence of counter pressure spikes in the pressure waveform, as shown in FIG. 12.

Figure 13:
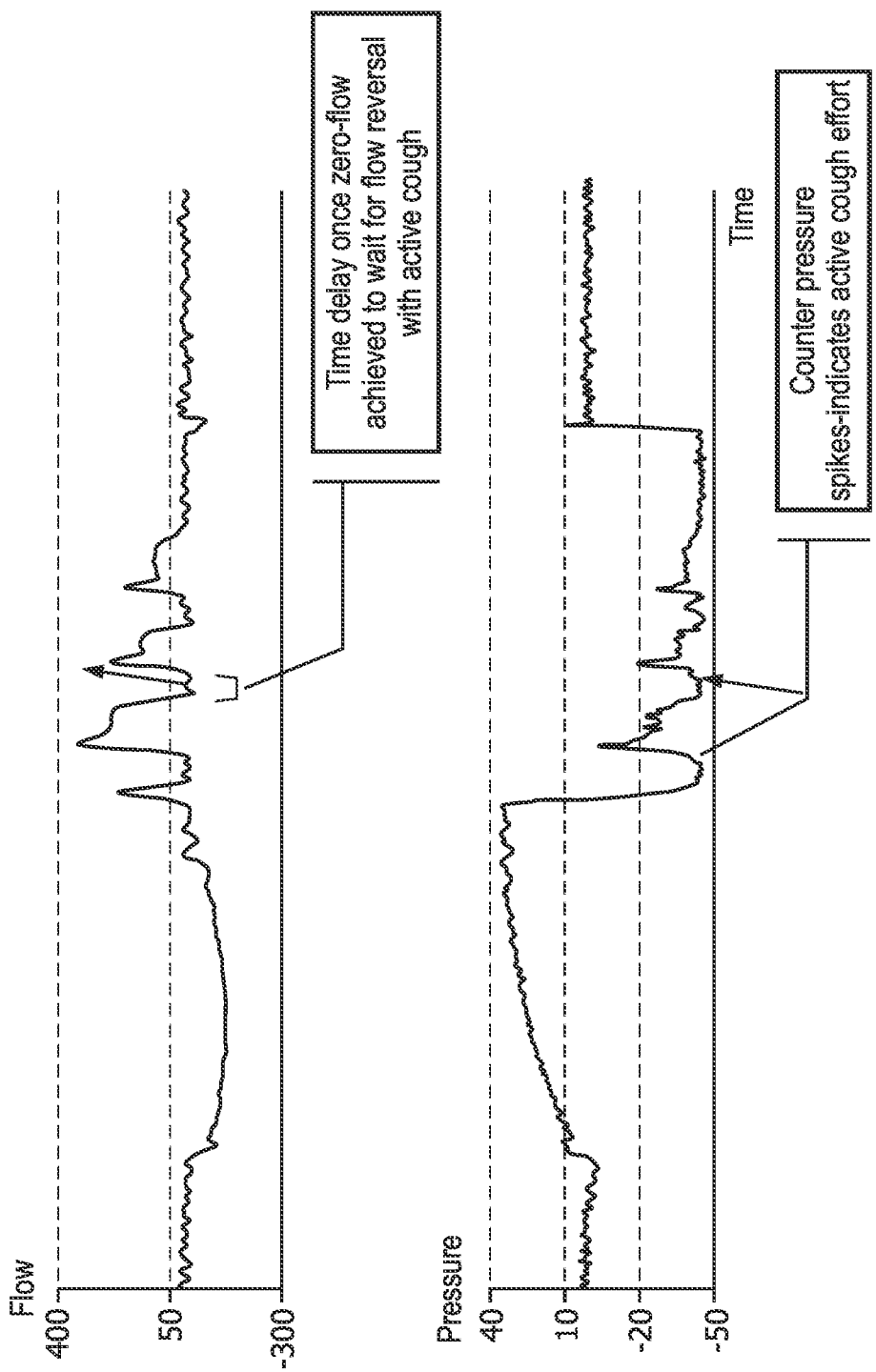

Counter pressure spikes would indicate an active cough effort with glottic closure, as shown in FIG. 13. In addition to the counter pressure spike detection, a pressure response delay could be introduced if zero flow is reached within the exhale phase to determine whether quick flow reversal (glottis opening, active cough effort) occurs. A flow reversal filter in the algorithm would prevent the fast pressure response algorithm from being triggered with an active cough effort and glottic closure even though a zero-flow point would occur during the exhale phase.

Figure 14:
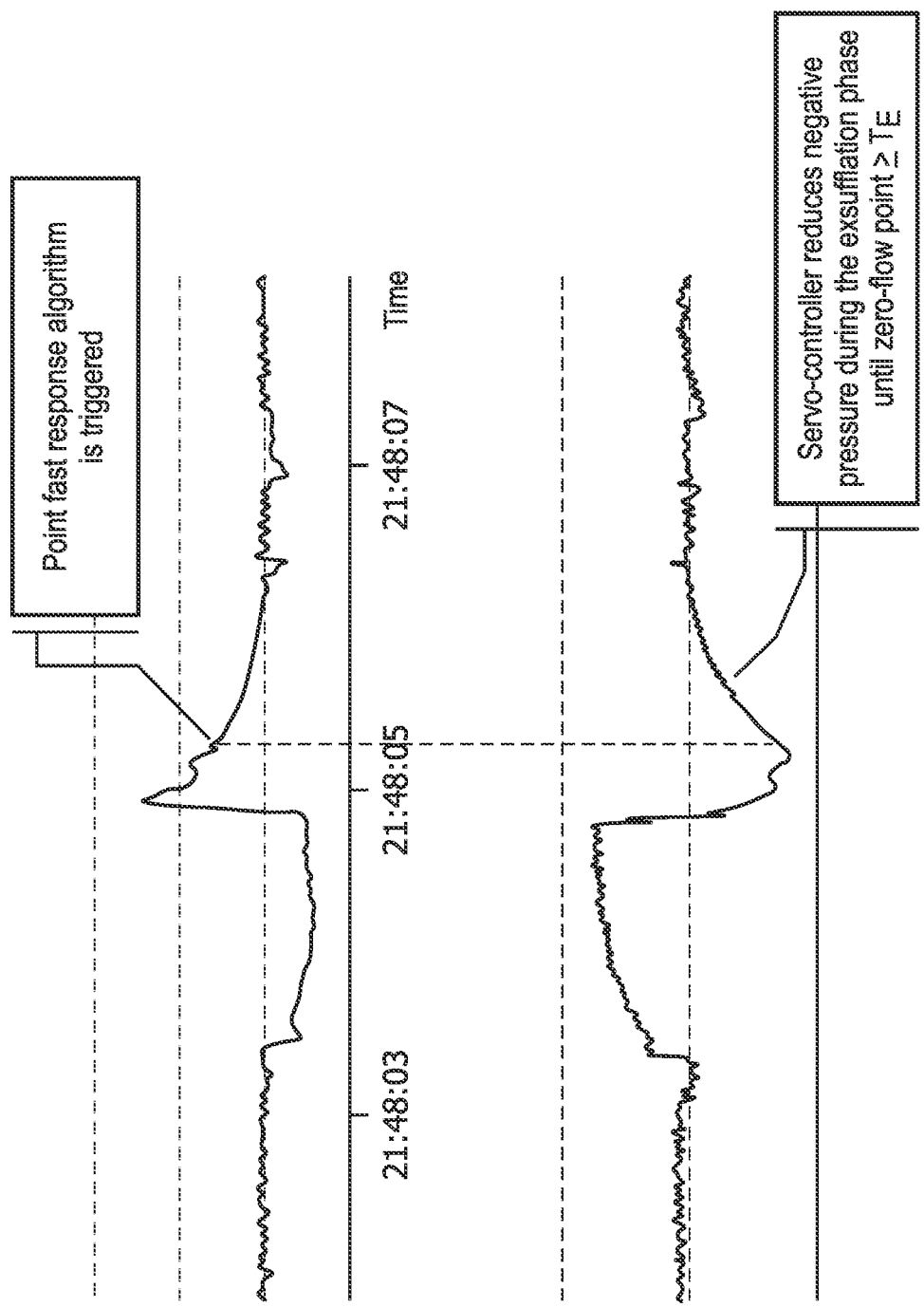

The fast response algorithm of the method 300 is a servo-controlled reduction in the delivered negative pressure setting for that exsufflation phase. The reduction in negative pressure is dependent upon the degree of exhale flow decay and prediction of the zero-flow point. The pressure reduction could be proportionate to the drop in PEFR or could continue to ramp to 0 $cmH_2O$ (ambient pressure) prior to the end of exsufflation. The fast pressure algorithm thus creates (3) different pressure profiles for a single mechanically assisted cough effort when triggered, as shown in FIG. 14.

Figure 15:
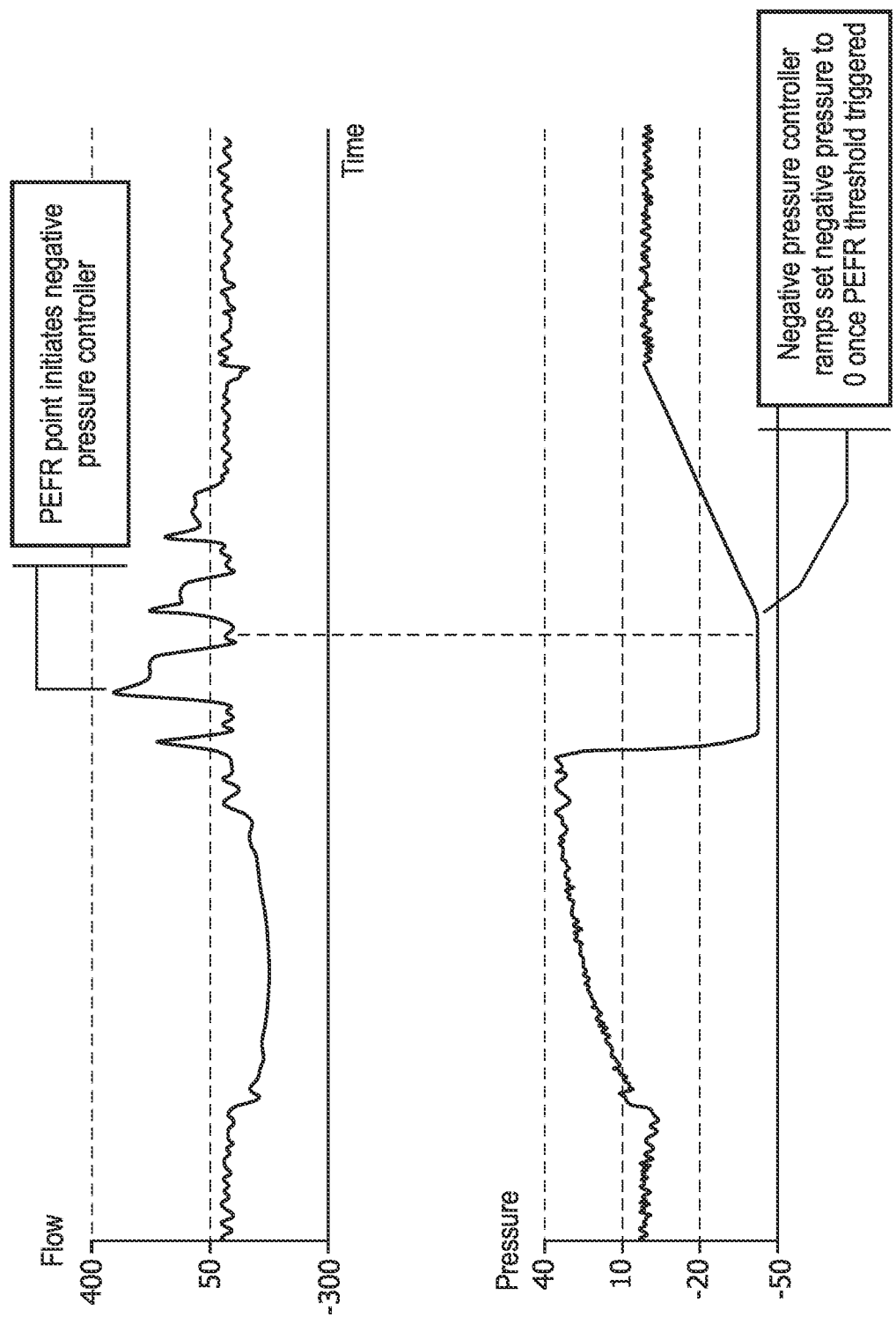

In another embodiment, the MI-E waveform would be modified from a bi-phasic (i.e., phase 1 being positive pressure and phase 2 being negative pressure) waveform into a tri-phasic waveform that would consist of a positive pressure during the inhale phase, followed by negative pressure delivered at the negative pressure setting during the initial portion of the exhale phase, that ramps to ambient pressure (i.e., 0 $cmH_2O$) by the end of the exsufflation phase once the PEFR is identified, as shown in FIG. 15.

Figure 16:
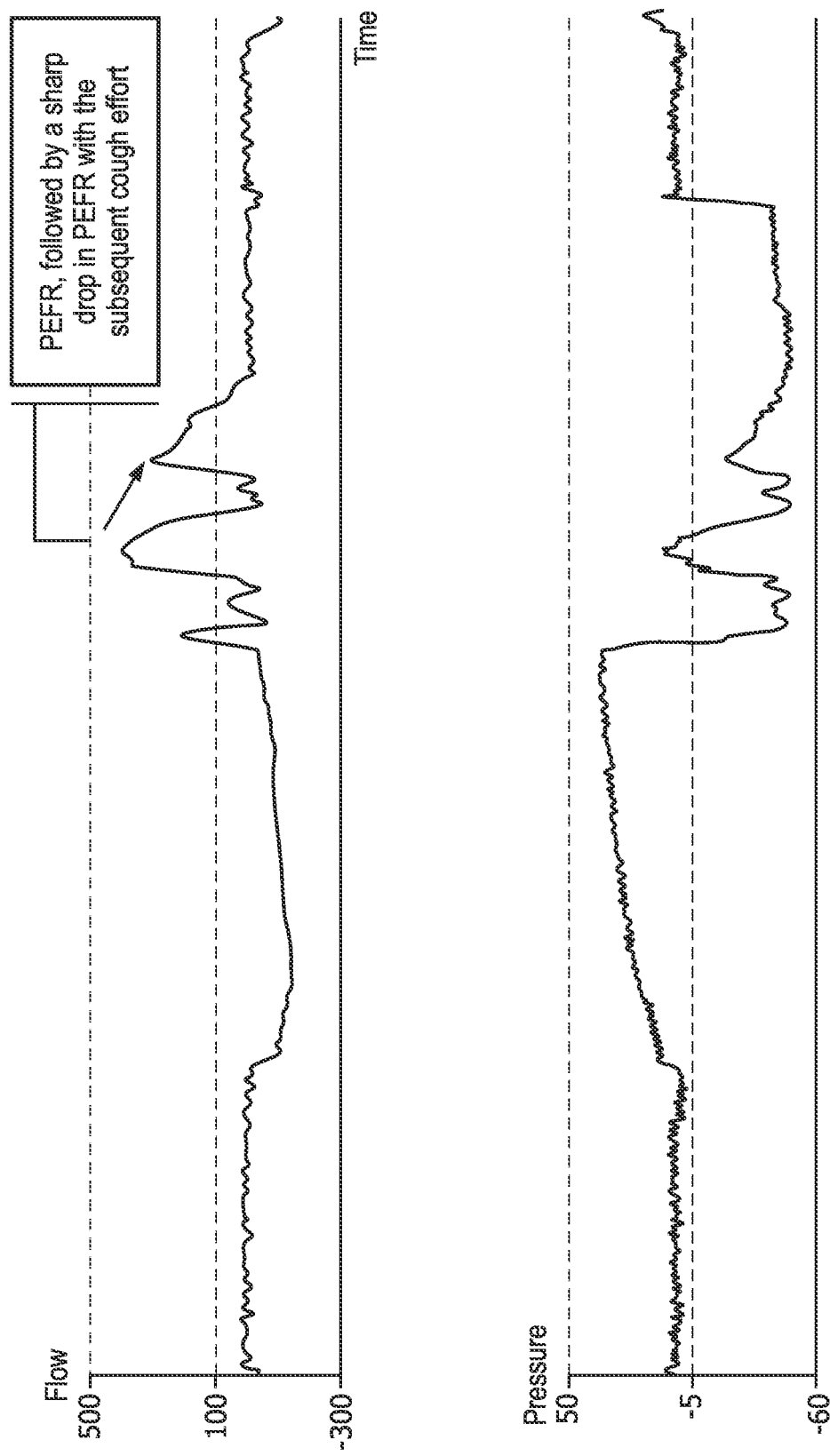

Fast reduction in negative pressure could be conceptually applied to all breaths provided that there will always be a decline in PCF value after initial PEFR with any subsequent patient cough efforts within a single mechanically assisted cough (MAC). The sharp decline in PCF with multiple patient cough efforts within a single MAC is caused by the significant drop in lung volume with each patient cough effort, as shown in FIG. 16. Fine tuning the exsufflation algorithm to focus on a single maximal PEFR and then ramping the negative pressure up to 0 $cmH_2O$ would serve as a protective mechanism to mitigate UA collapse, conceptually without impacting device efficacy. A PCF filter could delay the ramp in negative pressure until a PCF low threshold is reached (e.g. 160 lpm).

Figure 17:
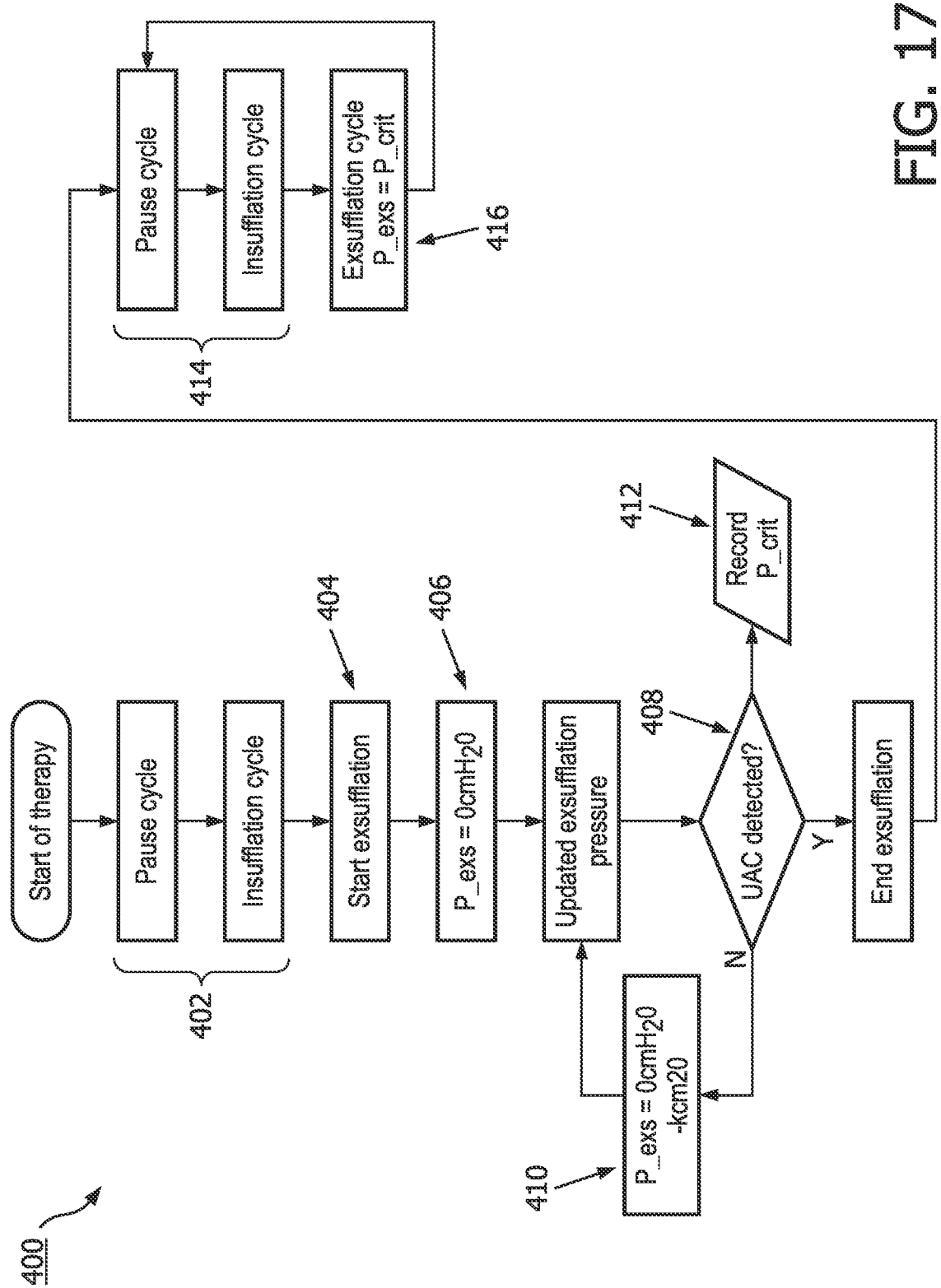
FIG. 17 shows another example flow chart of operations suitably performed by the system of FIG. 5.

With reference to FIG. 17, and with continuing reference to FIGS. 5 and 11, an example embodiment of the MI-E therapy method 400 is diagrammatically shown as a flow chart. The MI-E therapy method 400 is similar to the MI-E therapy method 300 except as described below.

At an operation 402, pressure is delivered to the patient P at a positive insufflation gauge pressure (similarly to the operations 104, 206 and 302).

At an operation 404, after the insufflation cycle, pressure is delivered to the patient P at a negative exsufflation gauge pressure (similarly to the operations 106, 208, and 304).

At an operation 406, a magnitude of the negative exsufflation gauge pressure to zero during the exsufflation cycle (similarly to the operation 202).

At an operation 408, the negative pressure delivery operation 406 continues until an UAC is detected (similarly to the operations 108, 210, and 306).

If no UAC is detected, then at an operation 410, a magnitude of the negative exsufflation gauge pressure is increased during the delivery of the exsufflation cycle. To increase the negative exsufflation gauge pressure, a constant value is added to the negative exsufflation gauge pressure by a constant k.

If an UAC is detected, then at an operation 412 the negative exsufflation gauge pressure is recorded as the negative exsufflation gauge pressure Pcrit for a subsequent MI-E cycle of the MI-E therapy method 400.

In addition, when an UAC is detected, a second cycle of the MI-E method 400 is performed, which includes an insufflation cycle operation 414 similar to the operation 402. Pressure is delivered to the patient P at the positive insufflation gauge pressure. At an exsufflation cycle operation 416, pressure is delivered to the patient P at the recorded negative exsufflation gauge pressure (from the operation 412).

Figure 18:
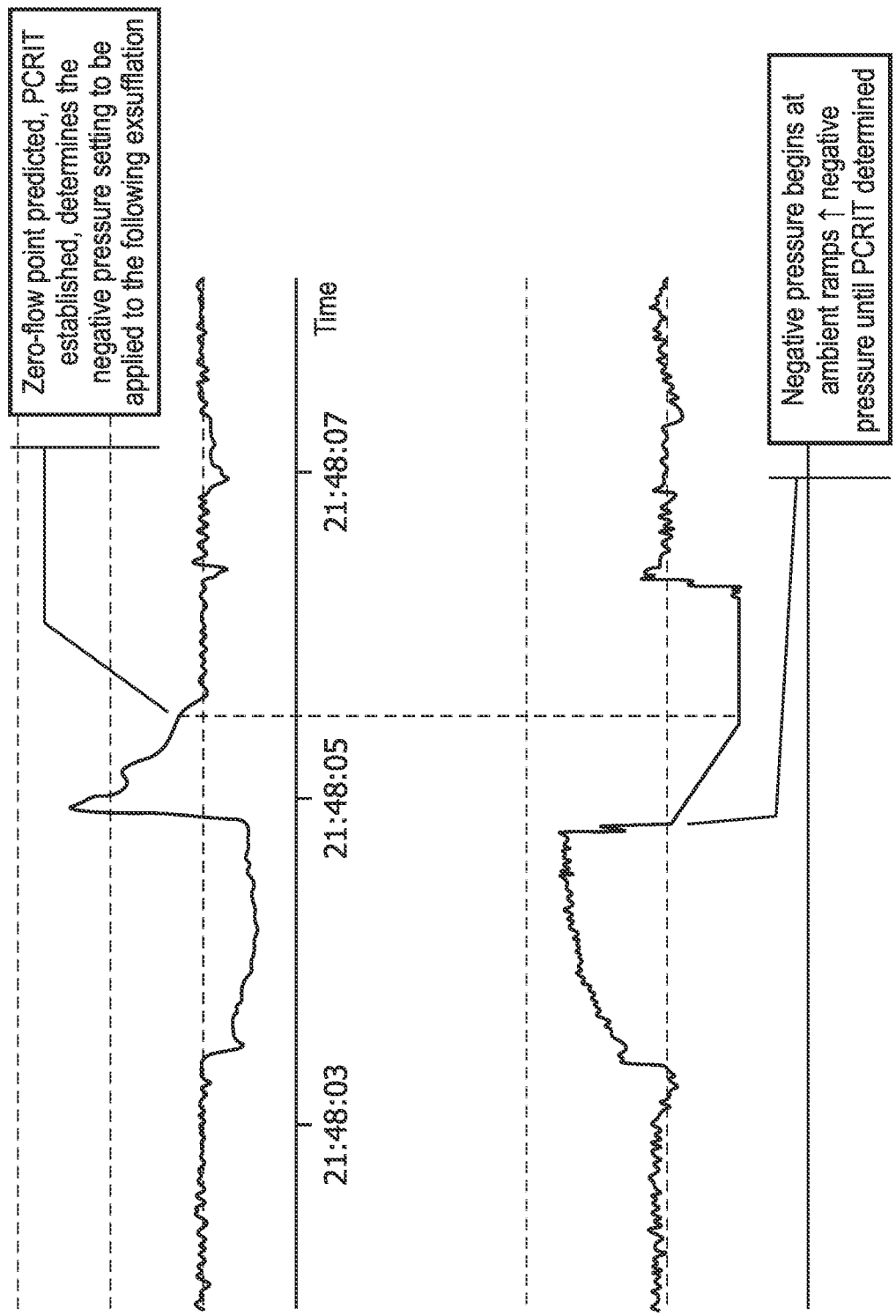
FIG. 18 shows flow and pressure curves for a patient undergoing the operations of FIG. 17.

The method 400 can be facilitated by introducing a Pcrit measurement tool. Clinical evidence reveals that Pcrit decreased (i.e., UA less collapsible) during peak inspiration and increased (i.e., UA more collapsible) during exhalation (see, e.g., Cao Y, McGuire M, Liu C, Malhotra A, Ling L: Phasic respiratory modulation of pharyngeal collapsibility via neuromuscular mechanisms in rats. J Appl Physiol 2012; 112(5): 695-703.). The Pcrit tool would thus be used during the exsufflation phase to determine and set the optimal negative pressure setting while avoiding a zero-flow point during exsufflation (UA collapse). Auto adjusting negative pressure would facilitate changes in disease state as the upper airway becomes more collapsible, resulting in the controller bringing the delivered negative pressure increasingly towards ambient. In the preferred embodiment, the patient would receive the target inhale pressure followed by a ramping of the negative exhale pressure beginning at ambient and decreasing toward the maximum negative pressure that could be applied within the constraints of the exhale time setting or until changes in the exhale flow pattern were noted to indicate UA compression. A series of evaluation breaths would facilitate increasing the peak negative pressure that was delivered up to the negative pressure ceiling (set inhale pressure setting) or until a zero-flow point occurs indicating the Pcrit value. The Pcrit value would be used to set the negative pressure setting (i.e., <target inhale pressure setting) for the next exsufflation phase, as shown in FIG. 18. A patient feedback tools such as mask seal and the detection of active effort (i.e., cough) during the exhale phase could further improve the effectiveness of the Pcrit negative pressure controller algorithm of the method 400.

An additional embodiment can include a primary function of preventing lung de-recruitment would be an automatic expiratory time control algorithm. Evaluation of the peak expiratory flow to determine the optimum time to cycle off the negative pressure would prevent exposure of the lung to unnecessary negative pressure after expiratory flow has decayed to zero. This feature may also aid in the prevention of UA collapse specifically for the patient that has initial expiratory flow with UA closure that occurs during the exhale phase. In the event that premature termination of the expiratory phase resulted in the development of intrinsic PEEP the overall risk to the patient is felt to be low as the intrinsic PEEP would be resolved as soon as the short MI-E therapy session concluded.

Referring back to FIG. 5, in order to perform the UAC or coughing detection processes described herein, the electronic controller 13 of the mechanical ventilator 2 can include a UAC detector module 16 and an Active Cough detector module 18. In particular, the UAC detector module 16 is programmed to perform the UAC detection operation 108 as described in more detail below.

Figure 19:
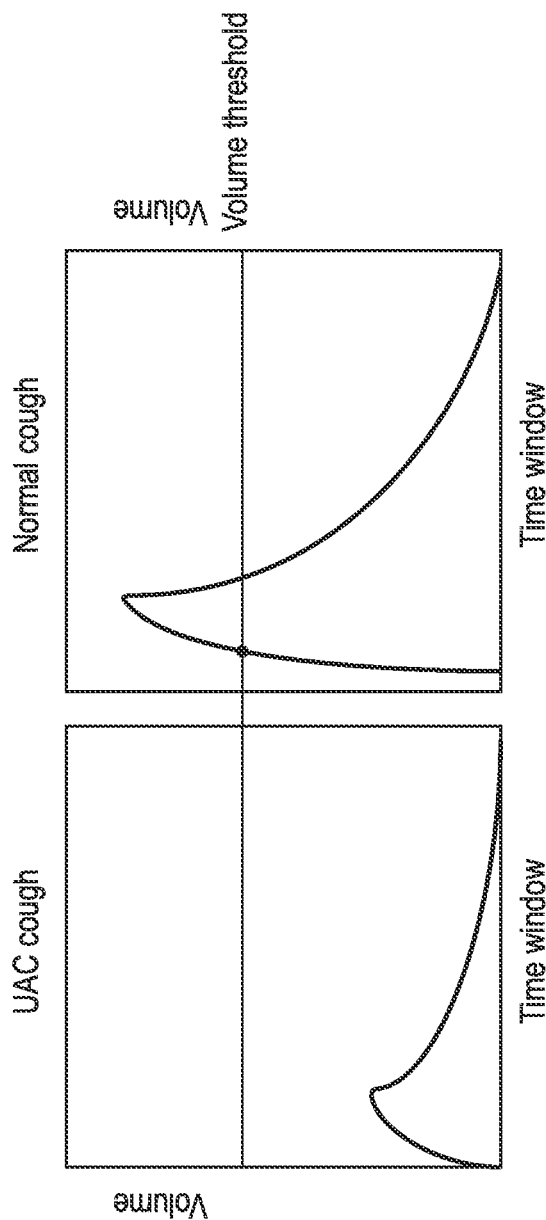
FIGS. 19-22 show curves for a patient produced by algorithms executed by a module of the system of FIG. 5.

The UAC detector module 16 is programmed to perform a flow threshold method, in which an exsufflation flow value is compared to an arbitrary minimum flow threshold within an arbitrary time window to determine an UAC condition. For example, as shown in FIG. 19, an arbitrary minimum flow threshold is set to 5% of peak cough flow within each cough cycle or 10 lpm, whichever is higher. An arbitrary time window is set to 30% of the set exsufflation time.

Figure 20:
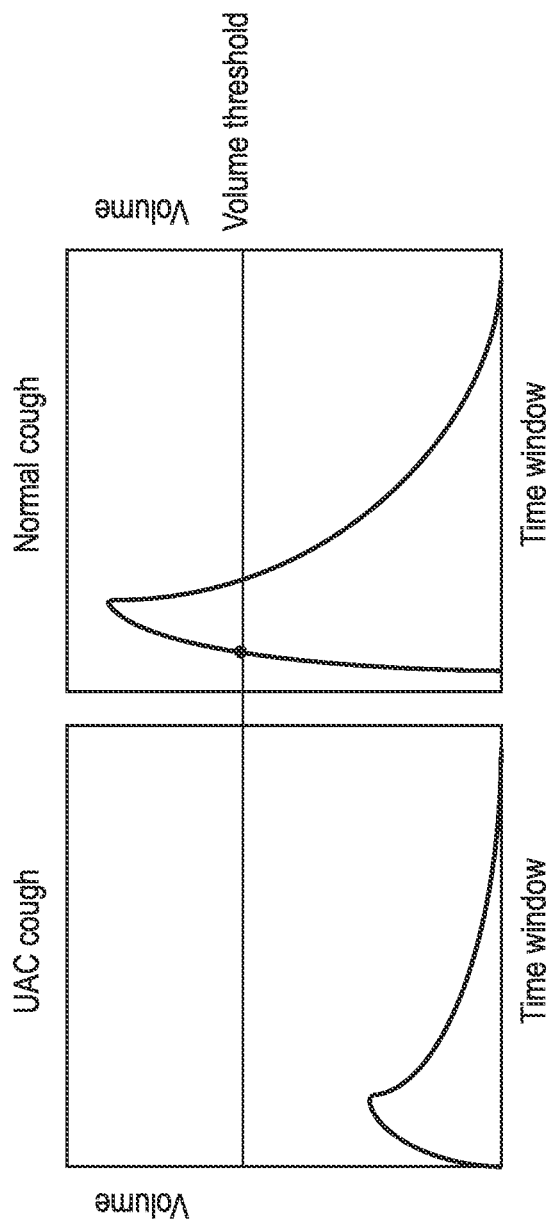

The UAC detector module 16 is programmed to perform a volume threshold method, in which an exsufflation volume is compared to an arbitrary minimum volume threshold within the entire exsufflation time or compared to the arbitrary fraction of the insufflation volume to determine an UAC condition. For example, as shown in FIG. 20, an arbitrary minimum exsufflation volume threshold is set to 50% of insufflation volume or 200 ml, whichever is greater.

Figure 21:
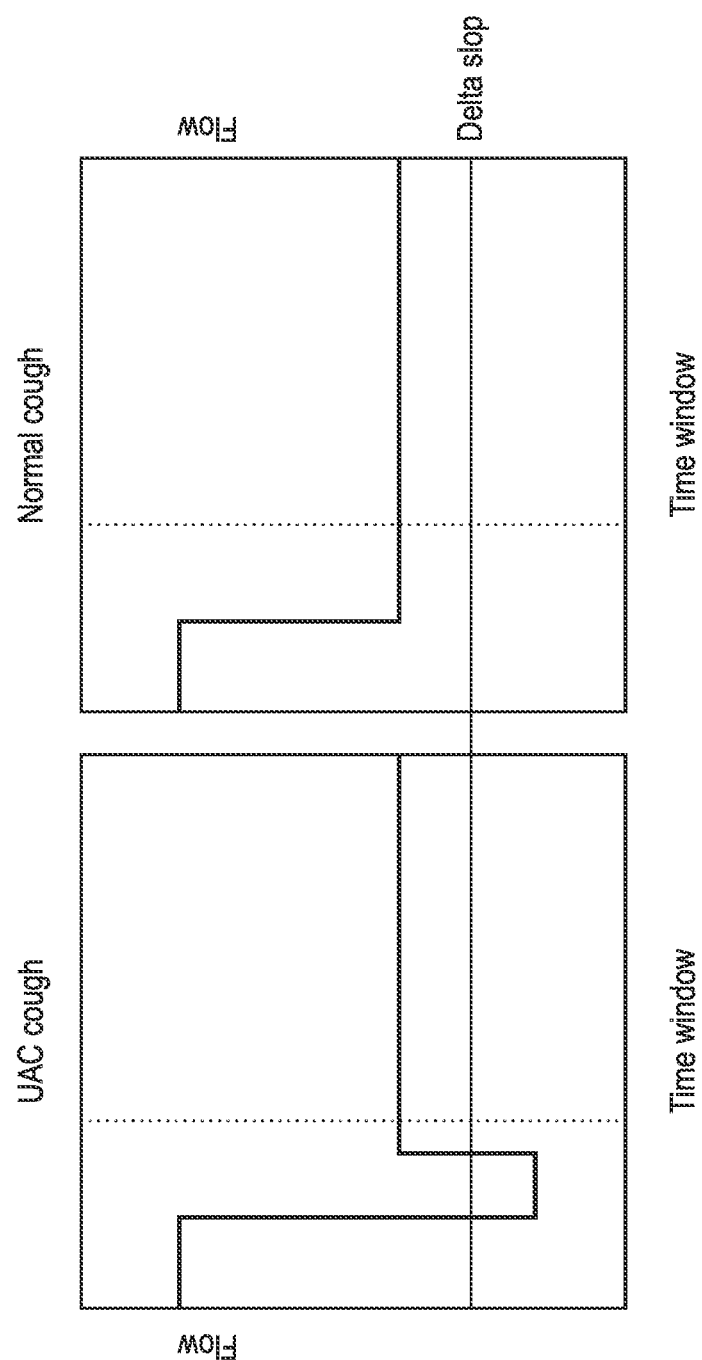

The UAC detector module 16 is programmed to perform a slope method, in which a change in flow over time is compared to an arbitrary maximum slope deviation threshold within an arbitrary time window to determine an UAC condition. For example, as shown in FIG. 21, an arbitrary flow slop deviation threshold is set to −0.25 or less. An arbitrary time window is set to 30% of the set exsufflation time.

Figure 22:
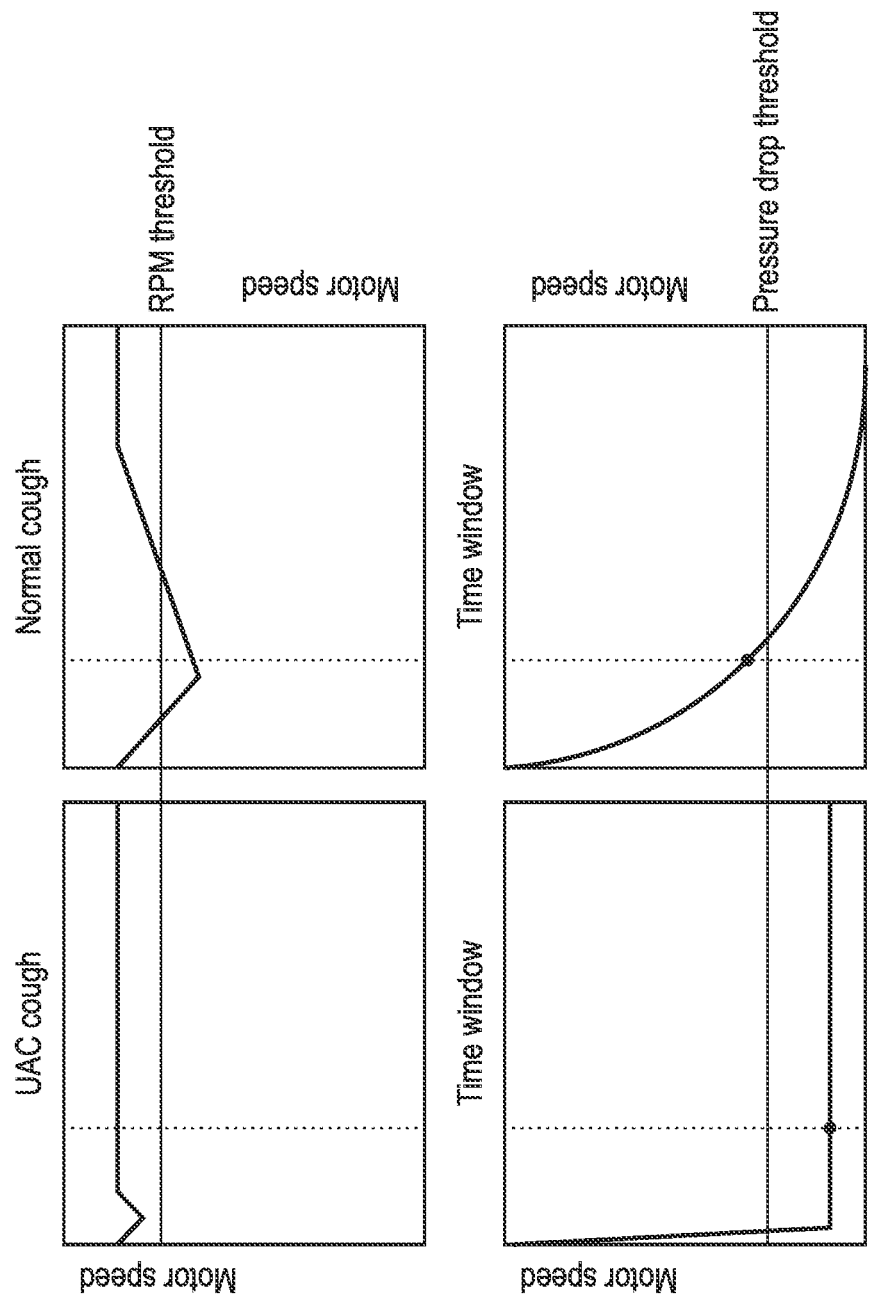

THE UAC detector module 16 is programmed to perform a revolution per minute (RPM) pressure deviation method, in which a change in RPM or pressure of the blower 12 (or flow generator source) over time is compared to an arbitrary maximum slope deviation threshold within an arbitrary time window to determine UAC condition. For example, as shown in FIG. 22, an arbitrary RPM threshold is set to 20,000 or 80% of set exsufflation pressure target. An arbitrary time window is set to 30% of the set exsufflation time.

THE UAC detector module 16 is programmed to perform a convolutional neural network (CNN) method employing artificial intelligence (AI) processes. Deeping learning and AI techniques have been used to classify various medical images. A CNN with a fully connected artificial neural network (ANN) is used to build a classifier to distinguish between a normal exsufflation waveform and the exsufflation waveform with an UAC. The sample M I-E waveforms for a CNN model can be supplied by either expert annotated real patient waveform data or a bench top airway model with a collapsible airway to simulate UAC. The following is an example of the CNN method using Python.

```
# Installing Theano
# Installing TensorFlow
# Installing Keras
// Cough waveform dataset preparation
// Create dataset folder structure with 1,000 M I-E cough
    cycle waveforms
    Training_Set (80%): Test_Set (20%)
    Normal_Cough: UAC
    NormalCough1.jpg . . . NormalCoughxx.jpg:
        UAC1.jpg . . . UACxx.jpg
# Building the CNN
# Importing the Keras libraries and packages
from keras.models import Sequential
from keras.layers import Convolution2D
from keras.layers import MaxPolling2D
from keras.layers import Flatten
from keras.layers import Dense
from keras.preprocessing.image import ImageDataGenerator
# Initializing the CNN
Classifier=Sequiential( )
# Convolution
Classifier.add (Convolution2D (32, 3, 3, input shape (64, 64, 1), activation='relu')
//32 feature detectors of 3×3, pixel size of 64×64 black
    and white
# Pooling
Classifier.add(MaxPooling2D (pool_size=(2, 2))
# Flattening
Classifier.add(Flatten( ))
# Full connection
Classifier.add(Dense(output dim=128, activation='relu')
// # of hidden nodes 128
Classifier.add(Dense(output dim=1, activation='sigmoid')
// binary output normal cough and UAC
# Compliing the CNN
Classifier.complie(optimizer='adam', loss='binary crosentropy', metrics=['accuracy']
// stochastic gradient descent, binary cross entropy, accuracy based performance
# Fitting the CNN to the images
train_datagen—ImageDataGenerator (rescale=1./255, shear_range=0.2, zoom_range=0.2, horizontal flip=True)
test_datagen=ImangeDataGenerator(rescale=1./256)
training_set=train_datagen.flow_from_directory ('dataset/training_set', target_size=(64,64), batch_size=32, class_mode='binary')
test_set=train_datagenflow_from_directory ('dataset/test_set', target_size=(64,64), batch_size=32, class_mode='binary')
Classifier.fit._generator (training_set, smaple_per_epoch='# of images', nb_epoch=25, validation data=test_set, nb_val sample='# of remaining samples')
# Additional convolution layers can be added to improve
    the accuracy of the model
```

The UAC detector module 16 is programmed to perform a forced oscillation technique (FOT) Delta Xrs method. An expiratory flow limitation can be determined with the respiratory impedance analysis. Under a normal airway patency during the exsufflation cycle, low frequency reactance measurements reflect the elastic properties of the respiratory system. During the UAC, a choke point is formed around the collapsible upper airway. The oscillatory signal cannot pass through this choke point, thus there is a marked reduction of the respiratory reactance, indicating the UAC. The following is an example of the FOT Delta Xrs method including selection of oscillatory frequency, sample methods, filtering, and mean calculation.

1. Mono-frequency of 6 Hz at 2 cmH$_2$O sinusoidal waveform is superimposed to M I-E therapy breath.
2. Pressure and flow signals are sample at 1024 Hz with 0.5 second window and 50% overlapping window, thus the resulting time resolution of 0.25 second.
3. Apply 4$^{th}$ order low pass filter at 25 Hz to remove noise.
4. Apply 6$^{th}$ order high pass filter at 2 Hz to remove the M I-E breath cycle.
5. Apply 6$^{th}$ order band pass filter +/−1 Hz of 6 Hz center frequency.
6. Apply FFT function to extract the coefficient at 4 Hz for each pressure and flow signal
7. Calculate Xrs (6 Hz)=FFT (Pressure)/FFT(flow) for insufflation cycle and exsufflation cycle
8. Calculate Delta Xrs is equals to the difference between Insufflation Xrs—exsufflation Xrs.
9. If delta Xrs is greater than e.g, 3cmH$_2$O/L/S, UAC is detected.

Along with delta Xrs, other parameters using FOT can be used to estimate the degree of the UAC: Zi, Ri, Xi, Ze, Re, Xe, Fr.

Zi: Insufflation respiratory impedance
Ri: Insufflation respiratory resistance
Xi: Insufflation respiratory reactance
Ze: Exsufflation respiratory impedance
Re: Exsufflation respiratory resistance
Xe: Exsufflation respiratory reactance
Fr: Resonance frequency The active cough detector module 18 is programmed to perform a flow-based oscillation detection method. For a flow based active cough effort detection, an AC coupled flow signal is analyzed. Various signal filtration schemes can be incorporated to improve the signal integrity. A dead time can be added at the beginning of the exsufflation phase to remove transient noise. The signal must cross a defined hysteresis band within an exsufflation time frame for the zero-crossing counter to increment. If the number of zero crossing in the signal is greater than an arbitrary number, then the active cough effort is detected. The zero-crossing sum is cleared at the start of each respiratory phase. The flow oscillation detecting process is depicted in FIG. 23.

The active cough detector module 18 is programmed to perform a pressure-based oscillation detection method. Similar to the flow based active cough effort detection method, ac couple pressure signal is analyzed. Various signal filtration schemes can be incorporated to improve the signal integrity. In this non limiting example, a band pass filter and signal rectification processes are adapted. A sum of the rectified signal is updated whenever the signal exceeds a specified minimum threshold. The active cough effort is detected when the summed signal exceeds a specified threshold. Pressure oscillations are cleared at the beginning of each respiratory phase. These outputs are shown in FIG. 24.

The active cough detector module 18 is programmed to perform a fast response UAC triggering method, which can be derived from the UAC detection method: Flow, volume, and flow slop method. The fast response UAC condition can be declared within the exsufflation time window, each flow, volume, and flow slop signals cross the arbitrary threshold.

The disclosed systems and methods provide a technique that for the first time makes the MI-E device clinically useful for supporting secretion clearance in neuromuscular patients that have bulbar symptoms. Prior to this the application of negative pressure was a significant deterrent in bulbar patients rendering the device ineffective.

The disclosed systems and methods support the complete removal of the negative pressure phase in very severe bulbar patients, thus preventing upper airway collapse. When maximum target inspiratory pressures are used to support MIC in combination with active expiratory efforts (i.e., coughing) then patients are much more likely to achieve PCF supportive of lung clearance. This use of the maximum target inspiratory pressure is in complete contrast to the current published recommendation to reduce inspiratory pressure in bulbar type patients. Reducing inspiratory pressure in this application is part of the strategy to reduce inspiratory flow and thus reduce inspiratory adduction in ALS and particularly bulbar ALS. However, if inspiratory flow control is successfully provided, then it would no longer be necessary to reduce the target inspiratory pressure as a method for reducing inspiratory flow. The flow controller 13 would allow inspiratory flow reduction to prevent inspiratory collapse, while at the same time permitting maximizing target inspiratory pressure to reach MIC. This should significantly improve PCF in the bulbar patient population.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A mechanical ventilation system, comprising:
   a mechanical ventilator configured to deliver ventilation to a patient; and
   an electronic controller programmed to control the mechanical ventilator to perform a mechanical insufflation-exsufflation (MI-E) therapy method including performing a MI-E cycle including:
   (i) during an insufflation cycle, delivering pressure to the patient at a positive insufflation gauge pressure;
   (ii) during an exsufflation cycle following step (i), delivering pressure to the patient at a negative exsufflation gauge pressure;
   (iii) determining, based on a presence or absence of a counter pressure spike during the exsufflation cycle, if a zero-flow point during the exsufflation cycle is caused by an active cough or an upper airway collapse; and
   (iv) reducing a magnitude of negative exsufflation gauge pressure for a subsequent exsufflation cycle if it is determined in step (iii) that the zero-flow point is caused by an upper airway collapse.

2. The mechanical ventilation system of claim 1, wherein the step (iv) reduces the magnitude of the negative exsufflation gauge pressure by a predetermined pressure magnitude decrease increment.

3. The mechanical ventilation system of claim 2, wherein the predetermined pressure magnitude decrease increment has a value of 5 cm $H_2O$.

4. The mechanical ventilation system of claim 1, wherein the therapy method is programmed to repeat until no upper airway collapse is detected.

5. The mechanical ventilation system of claim 1, wherein the therapy method comprises reducing the negative exsufflation gauge pressure to zero if the upper airway collapse is detected; and thereafter incrementally increasing the magnitude of the negative exsufflation gauge pressure.

6. The mechanical ventilation system of claim 5, wherein the incremental increase of the magnitude of the negative exsufflation gauge pressure proceeds until a second upper airway collapse is detected.

7. The mechanical ventilation system of claim 6, wherein the therapy method comprises, after detection of the second upper airway collapse, decreasing a magnitude of the negative exsufflation gauge pressure by a predetermined increment to a new negative exsufflation gauge pressure and maintaining the new negative exsufflation gauge pressure if an upper airway collapse is not thereafter detected.

8. The mechanical ventilation system of claim 7, wherein the therapy method comprises:
   decreasing a magnitude of the new negative exsufflation gauge pressure by using the predetermined pressure increment after an upper airway collapse is detected using the new negative exsufflation gauge pressure.

9. The mechanical ventilation system of claim 1, wherein the active cough comprises a glottis closure by the patient.

10. The mechanical ventilation system of claim 1, wherein the determining if a zero-flow point is caused by an active cough or an upper airway collapse comprises determining if the zero-flow point comprises one of at least two zero crossings during the exsufflation phase.

11. The mechanical ventilation system of claim 1, wherein the determining if a zero-flow point is caused by an active cough or an upper airway collapse comprises determining whether the zero-flow point is transient or associated with flow reversal.

\* \* \* \* \*